United States Patent
Heuring et al.

(10) Patent No.: US 9,572,915 B2
(45) Date of Patent: Feb. 21, 2017

(54) SYSTEMS AND METHODS FOR FLUID FLOWS AND/OR PRESSURES FOR CIRCULATION AND PERFUSION ENHANCEMENT

(71) Applicants: Jason J. Heuring, Houston, TX (US); William L. Clifton, Houston, TX (US); Benjamin A. Hertzog, Houston, TX (US); Michael P. Cuchiara, Houston, TX (US); Reynolds M. Delgado, III, Houston, TX (US)

(72) Inventors: Jason J. Heuring, Houston, TX (US); William L. Clifton, Houston, TX (US); Benjamin A. Hertzog, Houston, TX (US); Michael P. Cuchiara, Houston, TX (US); Reynolds M. Delgado, III, Houston, TX (US)

(73) Assignee: PROCYRION, INC., Houston, TX (US)

( * ) Notice: Subject to any disclaimer, the term of this patent is extended or adjusted under 35 U.S.C. 154(b) by 199 days.

(21) Appl. No.: 13/850,843

(22) Filed: Mar. 26, 2013

(65) Prior Publication Data
US 2014/0128659 A1    May 8, 2014

Related U.S. Application Data
(60) Provisional application No. 61/615,716, filed on Mar. 26, 2012.

(51) Int. Cl.
*A61M 1/10* (2006.01)
*A61M 1/12* (2006.01)

(52) U.S. Cl.
CPC ........... *A61M 1/1086* (2013.01); *A61M 1/101* (2013.01); *A61M 1/125* (2014.02)

(58) Field of Classification Search
CPC ............................ A61M 1/101; A61M 1/125
See application file for complete search history.

(56) References Cited

U.S. PATENT DOCUMENTS

| | | |
|---|---|---|
| 4,613,329 A | 9/1986 | Bodicky |
| 4,625,712 A | 12/1986 | Wampler |

(Continued)

FOREIGN PATENT DOCUMENTS

| | | |
|---|---|---|
| AU | 2005272610 | 2/2012 |
| EP | 2388029 | 11/2011 |

(Continued)

OTHER PUBLICATIONS
International Search Report for PCT/US2005/028875 dated Dec. 16, 2005.

(Continued)

*Primary Examiner* — Carl H Layno
*Assistant Examiner* — Jennifer Ghand
(74) *Attorney, Agent, or Firm* — Winstead PC

(57) ABSTRACT

Fluid pressure or flow in a human body may be adjusted with circulation or perfusion systems and methods. The system may include a first pump implantable in a chamber or vessel of the human body, and a plurality of struts connected to a housing of said first pump, wherein the struts secure the first pump in a desired location of the chamber or vessel. The system may also include one or more flow modification elements disposed on the first pump, where the flow modification elements direct flow to a desired organ or a desired vessel to adjust pressure or flow as desired.

14 Claims, 36 Drawing Sheets

(56) References Cited

U.S. PATENT DOCUMENTS

| | | |
|---|---|---|
| 4,919,647 A | 4/1990 | Nash |
| 5,207,695 A | 5/1993 | Trout, III |
| 5,405,383 A | 4/1995 | Barr |
| 5,911,685 A | 6/1999 | Siess et al. |
| 5,921,913 A | 7/1999 | Siess |
| 5,964,694 A | 10/1999 | Siess et al. |
| 6,116,862 A | 9/2000 | Rau et al. |
| 6,136,025 A | 10/2000 | Barbut et al. |
| 6,139,487 A | 10/2000 | Siess |
| 6,176,822 B1 | 1/2001 | Nix et al. |
| 6,176,848 B1 | 1/2001 | Rau et al. |
| 6,253,769 B1 | 7/2001 | LaFontaine et al. |
| 6,544,216 B1 | 4/2003 | Sammler et al. |
| 6,585,756 B1 | 7/2003 | Strecker |
| 6,610,004 B2 | 8/2003 | Viole et al. |
| 6,623,475 B1 | 9/2003 | Siess |
| 6,794,789 B2 | 9/2004 | Siess et al. |
| 7,027,875 B2 | 4/2006 | Siess et al. |
| 7,070,555 B2 * | 7/2006 | Siess ............... 600/16 |
| 7,144,364 B2 | 12/2006 | Barbut et al. |
| 7,473,220 B2 | 1/2009 | Francese |
| 7,708,771 B2 | 5/2010 | Chuter |
| 7,736,296 B2 * | 6/2010 | Siess et al. ............ 600/16 |
| 7,998,190 B2 | 8/2011 | Gharib et al. |
| 2003/0105383 A1 | 6/2003 | Barbut et al. |
| 2003/0176912 A1 | 9/2003 | Chuter et al. |
| 2003/0233143 A1 | 12/2003 | Gharib et al. |
| 2004/0044266 A1 | 3/2004 | Siess et al. |
| 2005/0220636 A1 | 10/2005 | Henein et al. |
| 2006/0036127 A1 | 2/2006 | Delgado, III |
| 2008/0103591 A1 | 5/2008 | Siess |
| 2010/0174131 A1 | 7/2010 | Foster et al. |
| 2011/0152999 A1 | 6/2011 | Hastings et al. |
| 2012/0041255 A1 | 2/2012 | Delgado, III |
| 2012/0088954 A1 * | 4/2012 | Foster ............... 600/16 |

FOREIGN PATENT DOCUMENTS

| | | |
|---|---|---|
| IT | 31466BE/2010 | 12/2010 |
| WO | 0033446 | 6/2000 |
| WO | 0110342 | 2/2001 |
| WO | 2005020848 | 3/2005 |
| WO | 2006/020942 | 2/2006 |
| WO | 2009/046779 | 4/2009 |
| WO | 2009/091968 | 7/2009 |

OTHER PUBLICATIONS

European Search Report, EP09175307.9, Dec. 18, 2009.
Rationale, Design and Methods for a Pivotal Rnadomized Clinical Trial of Continuous Aortic Flow Augmentation in Patients with Exacerbation of Heart Failure: The Momentum Trial, Journal of Cardiac Failure vol. 13, No. 9 2007, pp. 715-721.
International Search Report and Written Opinion for PCT/US2013/033894 dated Jun. 17, 2013.

* cited by examiner

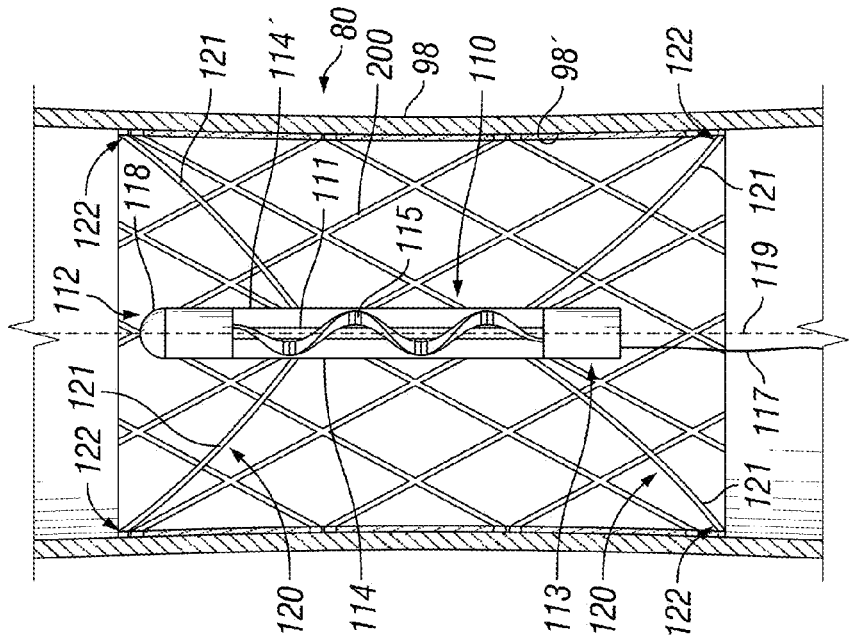
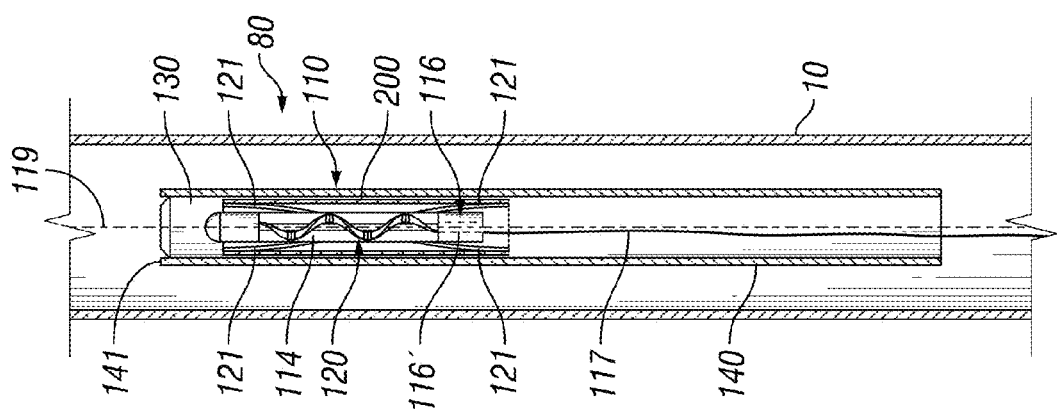

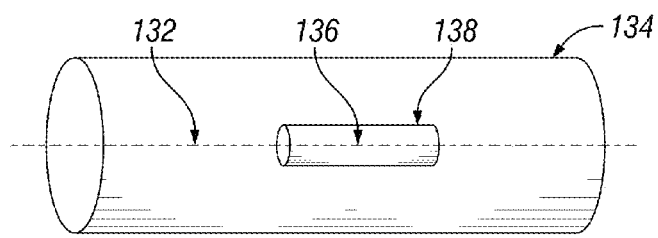 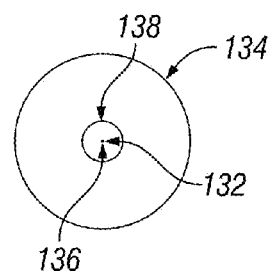
FIG. 12A-1  FIG. 12A-2
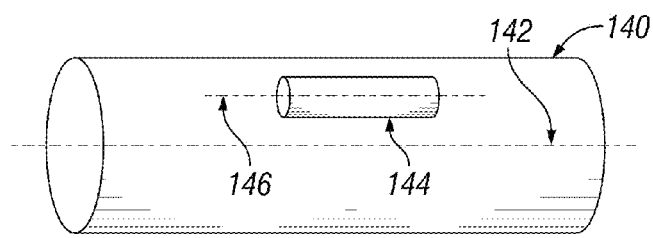 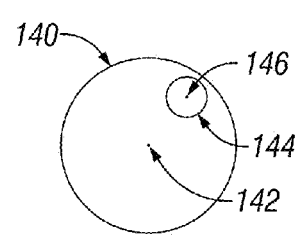
FIG. 12B-1  FIG. 12B-2
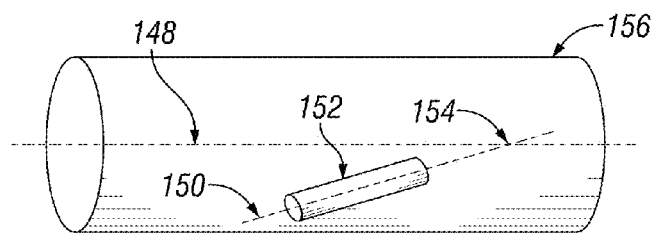 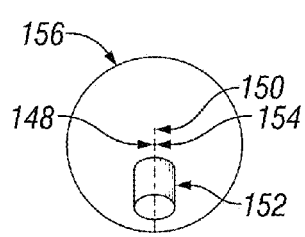
FIG. 12C-1  FIG. 12C-2
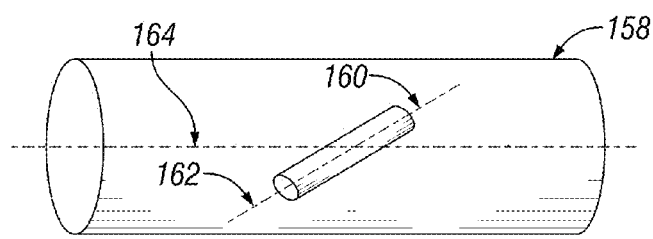 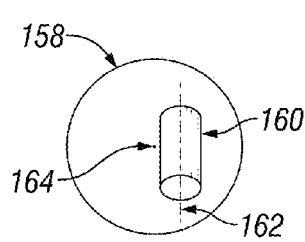
FIG. 12D-1  FIG. 12D-2

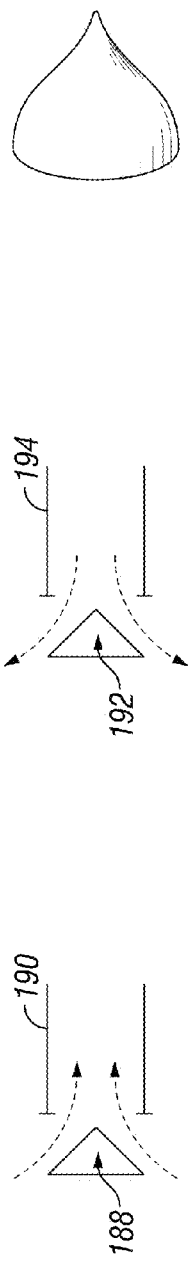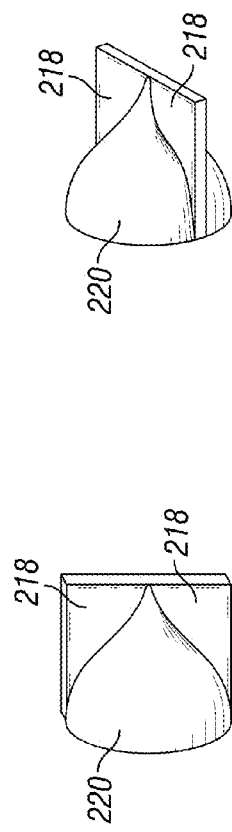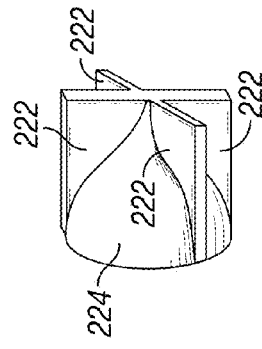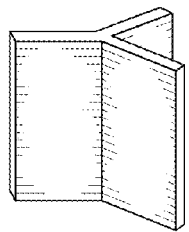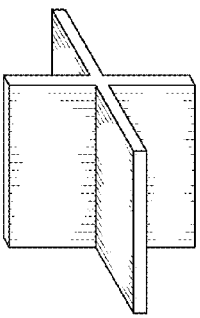

SYSTEMS AND METHODS FOR FLUID FLOWS AND/OR PRESSURES FOR CIRCULATION AND PERFUSION ENHANCEMENT

RELATED APPLICATIONS

This application claims the benefit and priority of U.S. Provisional Patent Application No. 61/615,716 filed Mar. 26, 2012, which is incorporated herein by reference.

FIELD OF THE INVENTION

This invention relates to a circulatory support system and method. More particularly, to systems and methods for vessel or end organ perfusion.

BACKGROUND OF INVENTION

Circulation and Perfusion Enhancement

Circulation of blood throughout the body and perfusion of end organs are basic functions in humans and most other animals. Many different problems and conditions result when this circulation is altered, obstructed, interfered with, or changed. Substantially all of the body is dependent on circulation for delivery of oxygen and nutrients and removal of waste products. If the pressure or flow rate of circulation to a certain organ or region of the body changes, that certain organ or region can experience loss of function, tissue death, or other impairment.

Some of the organs most dependent on optimal circulation are those that process the blood for the benefit of the entire body. For example, the kidneys, liver and spleen remove waste products or unneeded material from the blood. The small intestine transfers nutrients from consumed food to the blood. Changes to the circulation (also called perfusion) of these organs can have ill effects on the entire body.

Parts of the body that do not process blood for the benefit of the body also suffer from poor circulation. Peripheral vascular disease is characterized by poor circulation to the extremities. Symptoms include swelling, numbness, loss of function, pain, and tissue death. In serious cases, the affected limb or extremity can become gangrenous and amputation is required.

Methods for addressing poor circulation or perfusion include medications that increase the contractility of the heart (inotropes), reduce the fluid load on the heart to improve its function (diuretics), or open blood vessels to increase flow (vasodilators). These medications have disadvantages including, but not limited to, deleterious side-effects, habituation, partial effectiveness, or ineffectiveness. For example, inotropes can increase the risk of death. Diuretics and vasodilators interfere with some of the body's natural compensatory mechanisms, indicating their use involves some trade-off. For example, diuretics may reduce fluid load without actually addressing the underlying poor circulation that led to increased fluid load and vasodilators may increase flow but at reduced pressure (adequate perfusion requires adequate flow and pressure).

Mechanical devices are also used to improve circulation. Two classes of such devices are left ventricular assist devices (LVADs) and intra-aortic balloon pumps (IABPs). LVADs are pumps that are surgically implanted in the chest cavity and connected between the left ventricle of the heart and the aorta to augment the heart's output. IABPs are catheter based devices with a large balloon that inflates inside the aorta while the aortic valve is closed (i.e. during diastole) to force blood further into the circulatory system.

These mechanical devices have disadvantages also. LVAD implantation requires major open heart surgery in a well-equipped operating room and has a lengthy recovery period (forty days or more). Total cost for the procedure can range from a few hundred thousand to a million dollars or more. Additionally, serious complications (e.g. stroke or infection) from the procedure are common. IABPs are safer, but usually limited to short-term in-hospital use. In addition, the effectiveness of an IABP is directly related to the size of the balloon and larger balloons can extend past branches off the aorta (e.g. the phrenic, superior mesenteric, celiac, and renal arteries) that supply blood to several key organs. In this case, these organs may see only limited improvement (or even reduction) in circulation.

In addition to the disadvantages described above, medications, VADs, and IABPs provide systemic level circulatory support that is difficult or impossible to adjust in magnitude or limit to or localize in or focus on a particular organ, area, region, or part of the body. Drug therapy takes some time to have significant impact and is not practical for emergency or acute or short term improvement to circulation or perfusion. LVADs are also not practical for emergency or acute or short term improvement to circulation or perfusion due to the expense, invasiveness, planning, and time required for LVAD implantation.

One helpful context in which to judge, without limiting, the advantage of a system for creating specific enhancements to circulation and perfusion over blood pumps delivering non-specific systemic support is in the treatment of shock.

When a person's tissues are starved of oxygen rich blood over time, the person may enter a state of shock. Shock, usually caused by sepsis, hemorrhage, or acute heart failure, causes millions of deaths per year. Over half of shock patients die, usually as a result of multiple organ failure (MOF). The kidneys are at the root of multiple organ failure: poor perfusion of the renal arteries begins a dangerous feedback loop that can lead to damage of numerous organ systems.

For this reason, prevention of end organ failure is most often focused on supporting the kidneys. Traditional treatments include pharmacologic therapies, IV fluid optimization, vasopressors, and eventually renal replacement therapy (e.g. dialysis). Current therapeutic guidelines have not changed in decades, despite the fact that no pharmacologic treatment has been proven effective in clinical trials and excessive IV fluid burden can cause peripheral and pulmonary edema. Furthermore, the use of pressors to increase blood flow to the kidneys can cause acute and permanent ischemic damage to extremities and other organs.

Mechanical cardiovascular or circulatory support (MCS) to increase blood flow and pressure to the kidneys and/or other end organs is a novel approach to the treatment of shock. Current MCS treatment devices or methods are generally targeted at supporting the coronary vasculature during acute periods of cardiogenic shock, such as following a myocardial infarction or during percutaneous coronary intervention. Among these current approaches, a device that can be configured, without limitation, to deliver specific enhancements in circulation and perfusion, e.g., to improve renal clearance, would be an indispensable tool for cardiovascular or circulatory support.

The systems and methods discussed herein provide cardiovascular support, configurable flow and pressure management, and selective perfusion of specific targeted vessel(s) and end organ(s). Non-limiting examples of uses may include increasing renal perfusion to treat acute/chronic kidney injury; treating cardiogenic, septic, hypovolemic, or hemorrhagic shock; changing carotid perfusion to avoid ischemic stroke or balance the effect of downstream pumps; changing celiac/mesenteric perfusion to treat obesity or bowel ischemia; increasing liver perfusion to treat liver disease; improving perfusion of the heart itself by pulling blood from the coronary sinus, pushing blood into the coronary sinus, or pushing blood into the coronary arteries; and/or diverting flow away from sources of bleeding.

SUMMARY OF THE INVENTION

In one embodiment, a system for adjusting pressure of flow in a human body may include a first pump implantable in a chamber or vessel of the human body, and a plurality of struts connected to a housing of said first pump, wherein said struts secure the first pump in a desired location of said chamber or vessel. The system may also include one or more flow modification elements disposed on said first pump, where said flow modification elements direct flow to a desired organ or a desired vessel to adjust pressure or flow as desired. In some embodiments, the system may provide one or more additional pumps. The position or orientation of the pumps and flow modification elements may be oriented to assist native flow, increase or decrease pressure in a region, direct flow in a direction opposite of native flow, direct flow towards desired vessel(s) or organ(s), or a combination thereof.

In another embodiment, a method for adjusting fluid flow or pressure within a human body is provided. The method may include transluminally inserting a pumping system in a desired chamber or vessel the human body. The pumping system a pump, a plurality of struts, and one or more flow modification elements. The method may also include deploying said plurality of struts to secure said pumping system in the desired chamber or vessel. In some embodiments, the pumping system may provide one or more additional pumps. The position or orientation of the pumps and flow modification elements may be oriented to assist native flow, increase or decrease pressure in a region, direct flow in a direction opposite of native flow, direct flow towards desired vessel(s) or organ(s), or a combination thereof.

The foregoing has outlined rather broadly various features of the present disclosure in order that the detailed description that follows may be better understood. Additional features and advantages of the disclosure will be described hereinafter.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein:

FIG. 1F is a partial cross-sectional view of another embodiment of the intravascular pumping module of the present invention in a first transluminal delivery configuration, the device being enlarged for clarity;

FIG. 1G is a partial cross-sectional view of another embodiment of the intravascular pumping module in accordance with the present invention in a second deployed configuration;

FIGS. 12A-1 to 12D-1 and 12A-2 to 12D-2 are illustrative embodiments of axiosymmetric (a), axis-parallel (b), axis-intersecting (c), and skew orientations of devices in a vessel (d);

FIGS. 24a-24i are illustrative embodiments of various outlet port nozzles;

FIGS. 25a-25g are illustrative embodiments of various flow directors;

DETAILED DESCRIPTION

Figure 1A:
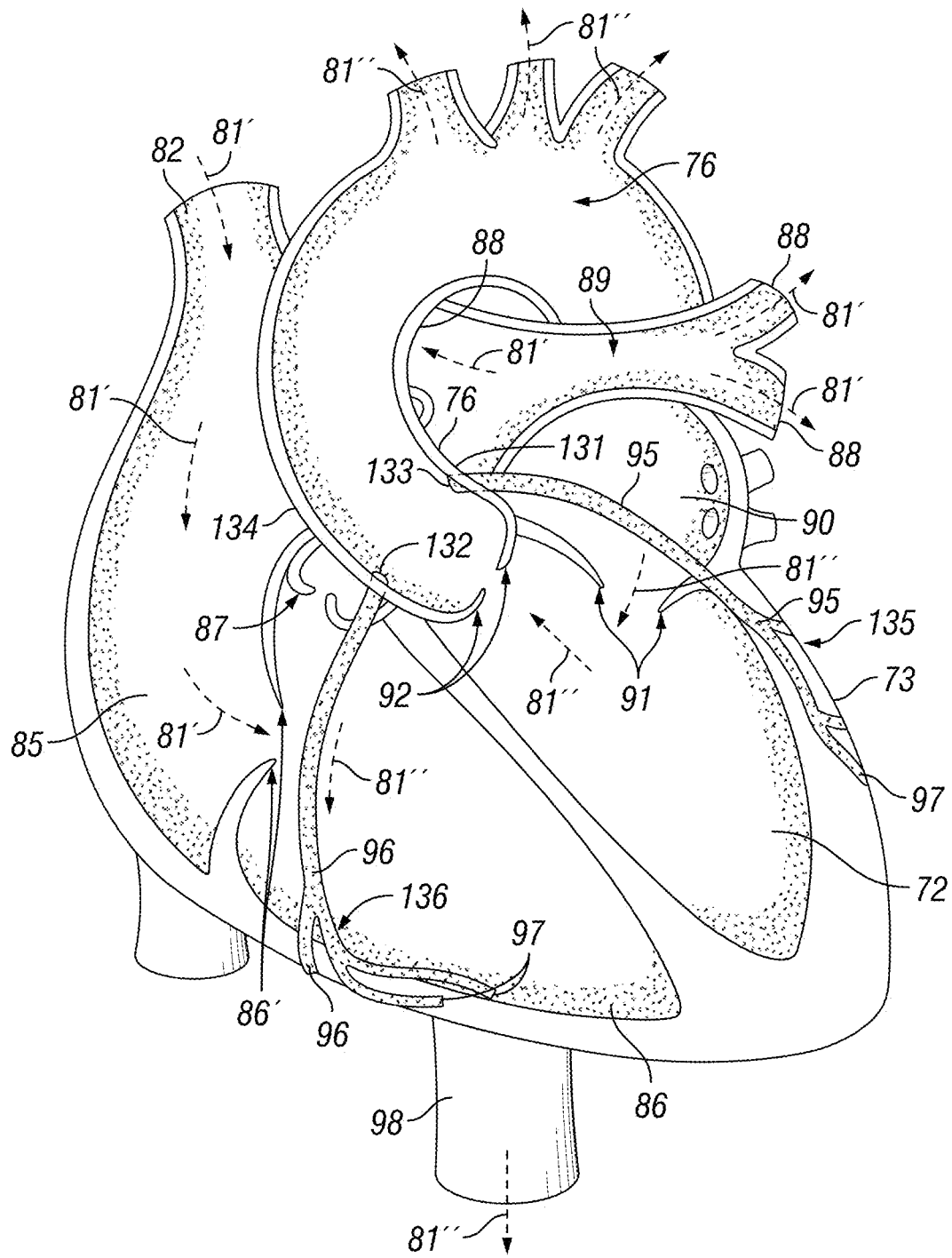
FIG. 1A is a partial cross-sectional view of a heart, to illustrate its functions and anatomy.

Refer now to the drawings wherein depicted elements are not necessarily shown to scale and wherein like or similar elements are designated by the same reference numeral through the several views.

Referring to the drawings in general, it will be understood that the illustrations are for the purpose of describing particular implementations of the disclosure and are not intended to be limiting thereto. While most of the terms used herein will be recognizable to those of ordinary skill in the art, it should be understood that when not explicitly defined, terms should be interpreted as adopting a meaning presently accepted by those of ordinary skill in the art.

It is to be understood that both the foregoing general description and the following detailed description are exemplary and explanatory only, and are not restrictive of the invention, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise.

Systems and methods for series modification of flow and/or pressure to create circulation of perfusion enhancements targeted to specific vessels and/or end organs are discussed herein. The systems and methods allow for managing the flow and/or pressure of fluids to create specific circulation or perfusion enhancements in one or more vessels or chambers of the human body by utilizing one or more pumps implanted within chambers or vessels of the human body. This is series flow augmentation, accomplished within the vasculature and without creating alternative or parallel flow paths.

This application describes systems and methods for using intravascular blood pumps, together with novel flow and pressure modification elements, to selectively augment, control and/or adjust the perfusion of targeted branch vessel(s) and/or end organ(s) in specific ways. An exemplary embodiment of such an intravascular blood pump is described in U.S. Pat. No. 8,012,079, which is incorporated by reference herein. A nonlimiting embodiment of a circulation and perfusion enhancement system may comprise such an intravascular blood pump fitted with flow and pressure modification elements and secured to the wall of a vessel or lumen or chamber with a securing means. In a nonlimiting embodiment, the circulation and perfusion enhancement system is disposed along the central axis of the vessel or lumen or chamber without significantly blocking the path of native blood flow. The securing means may extend from the pump and/or flow and pressure modification elements to secure the pump and flow and pressure modification elements to the wall of a vessel or lumen. This securing means also does not significantly obstruct native blood flow as it passes around the circulation and perfusion enhancement system.

The circulation and perfusion enhancements created by the circulation and perfusion enhancement system can be well specified along a number of dimensions. Without limitation, the circulation and perfusion enhancements the circulation and perfusion enhancement system may create include increased or decreased fluid flows of various velocities and in various directions, flows that are turbulent or laminar, flows that mix quickly or slowly with native blood flow, flows that are targeted for specific end organs, regions of increased or decreased pressure that may be diffuse or tightly focused, or a combination thereof.

In addition to the ability to achieve specific and defined enhancements to circulation and perfusion, the circulation and perfusion enhancement system design and size allow freedom of placement in many vessels or chambers of the body. These characteristics give the circulation and perfusion enhancement system distinct advantages over other mechanical circulatory support options.

Active and Ambulatory Patient Recovery: Surgically implanted VADs are one potential option for patients with cardiogenic shock unresponsive to inotropic therapy. However, their use has been limited by the risks associated with implantation and the cost of current devices. VADs require a long, technically complex, open heart surgery with added risk of death, injury, and infection. Furthermore, only a small number of specialized medical centers with experienced surgeons can properly implant these pumps. At the other end of the spectrum, percutaneous mechanical cardiovascular or circulatory support (MCS) devices are less invasive, but do not allow for patient ambulation and are not fully implantable.

In some embodiments, the systems and methods discussed herein may allow a pump to be deployed through a catheter percutaneously or by minor surgical access to the vasculature. In some embodiments, the systems and methods provide a fully implantable cardiac assist device due to the ability to use an implantable battery and transcutaneous charging. Since there will be no indwelling leads or open surgery, the patient will have the ability to ambulate early in recovery, which has been shown to significantly decrease recovery time and length of stay. In some embodiments, the system may be anchored by struts in its safe location (i.e. downstream of the carotids and away from organs and valves) in the descending aorta or other vessel locations to provide stability that allows for patient mobility and ambulation. In contrast, IABPs have unanchored positioning and intracardiac percutaneous VADs are positioned across the aortic valve. Devices with a pneumatic or mechanical driveline have a risk of vessel injury or kinking or loading the line with patient movement. The systems and methods discussed herein provide a fully implantable design that reduces or avoids these risks and allows for faster patient recovery.

Safety: In some embodiments, the system is deployed in a specific location in the descending aorta or one of its branch vessels (e.g. the celiac, superior mesenteric, renal, inferior mesenteric, gonadal, iliac, or subclavian) away from the heart or end organs and downstream of the carotid arteries. For example, in a nonlimiting embodiment, the pump may be inserted from a femoral or iliac site and deployed in the descending thoracic aorta. Such deployment positions of the systems and methods downstream of the carotids discussed herein have drastically reduced risks compared to other blood pumps that discharge upstream of the carotids or that are deployed across the aortic valve into the left ventricle and/or upstream of the carotids. Placement upstream of the carotids drastically reduces the chance of our system causing an embolic stroke or the like. Avoiding placement across the aortic valve is safer for use in patients with valvular disease and carries a lower risk of damaging the native valve. In some embodiments, the system may be delivered via catheter with a single access site at or near the femoral or iliac or other major artery or vein. Compared to the risky open heart procedure for traditional VADs or the atrial septum puncture required by other less-invasive VADs, complication rates should be greatly reduced. Further, the system takes up only a fraction of the cross sectional area of the aorta and allows blood flow around the device, thereby greatly reducing risks that may arise from pump failure. The system's small cross sectional area also allows interventionists to perform simultaneous cardiac catheterization procedures via the femoral access site by passing catheters around our system while it is in place and functioning.

Hemodynamics & Function: In one embodiment, the system is positioned immediately proximally to the renal and mesenteric arteries and increases both systolic and diastolic pressure and flow to these vessels while preserving the native pulsatile flow waveform (which may produce healthier perfusion than VADs that eliminate pulsatility which sometimes see conditions like acquired von Willebrand syndrome and gastric bleeding). In this embodiment, the system creates a pressure gradient that causes both cardiac load reduction and a constant increase in both pressure and flow downstream to key end organs, including the kidneys. IABPs, on the other hand, modify aortic pressure to reduce cardiac load during systole, but may actually decreases mean arterial pressure (MAP) to end organs. The system is simpler than IABPs in that no electrocardiography (ECG) sync is required. This functionality, in addition to our continuous flow design, makes the system uniquely suitable for patients with tachyarrhythmia or atrial fibrillation. Traditional, less invasive, and intra-cardiac percutaneous VADs work in parallel with the left ventricle, taking over a large percentage of the cardiac output. These devices increase cardiac load, making it more difficult for the heart to naturally eject blood through the aortic valve. Our system functions in series with the heart, meaning the heart still ejects the total cardiac output naturally across the aortic valve, but with the assistance of our device. This assistance may manifest as increased cardiac output, increased ejection fraction, reduced afterload, reduced aortic root pressure, the aortic valve opening earlier in the cardiac cycle and remaining open longer during the cardiac cycle, and/or reduced work of the heart. These simply achieved but significant flow and pressure benefits will also be present in non-aortic placements of our device.

To summarize, some advantages of the circulation and perfusion enhancement system over traditional or less-invasive surgical VADs are ease of insertion (no surgeon, operating room, or OR-type sterile conditions required), speed of insertion (minutes not hours), non-invasiveness (low risk, low stress on possibly old or injured body), lower stroke risk (downstream of carotids), greater suitability for TET (which provides lower infection risk), maintained pulsatility, unobstructed native blood flow (which can flow right around the device if it partially or completely fails), specificity of circulation or perfusion enhancement, and greater suitability for short term use.

Some advantages of the circulation and perfusion enhancement system over intracardiac percutaneous VADs are no hardware across the aortic valve, no hardware in the heart, higher suitability for long term use, lower stroke risk, and specificity of circulation or perfusion enhancement.

Some advantages of the circulation and perfusion enhancement system over IABPs are more control over pressure profile (can alter systolic and diastolic pressures without affecting flows), smaller size (less occlusion of vertebral and renal and mesenteric and celiac arteries; large size of balloon makes enhanced perfusion of these arteries difficult to predict and control), potential for long term use, and no reduction of MAP or flattening native hemodynamics.

Figure 8A:
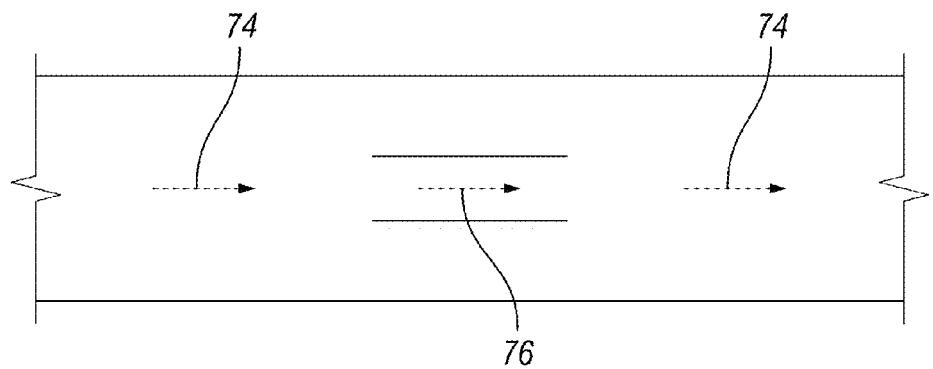
FIGS. 8a and 8b are illustrative embodiments of a series flow augmentation (a) and a parallel flow augmentation (b)
Figure 8B:
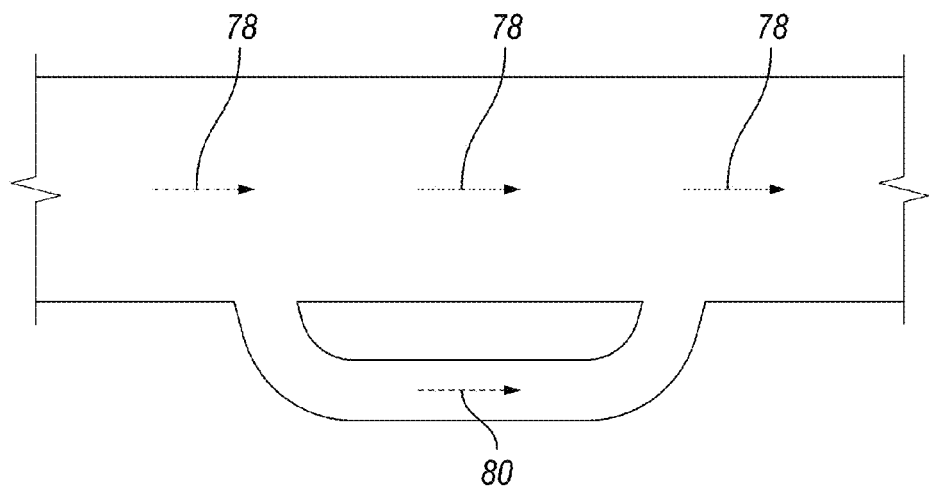

The circulation and perfusion enhancement system acts through series flow augmentation. This is the case where the entire device lies inside the vessel or chamber and no alternative or parallel flow path is created or used. FIGS. 8*a* and 8*b* illustrates the difference between (a) series flow augmentation and (b) parallel flow augmentation. In series flow augmentation (FIG. 8*a*), the pumped flow (76) physically takes the place of a portion of the native flow path (74) in some part of the vessel or chamber. In parallel flow augmentation (FIG. 8*b*), the pumped flow (80) is separate and apart from the native flow path (78) and does not physically take the place of any part of the native flow path (78). In general, parallel flow augmentation is more complicated, since the alternative flow path must be established. In addition, areas were native blood flow is artificially split and recombined tend to be thrombogenic.

The circulation and perfusion enhancement system can produce a variety of hemodynamic effects including, without limitation, large or small increases in flow that are laminar or turbulent, guided in a desired direction, with high or low velocity, and with or without swirl; flows or pressure gradients opposite the physiological norm; and large or small increases or decreases in pressure that are diffuse or tightly focused. These effects can be leveraged to produce swirl in the main vessel or increase or decrease perfusion (which is a function of flow and pressure) through various branch vessels or to specific end-organs. Swirl may stimulate the endothelium to release, NO and other compounds that improve the arterial tone and reduce SVR. Changes in perfusion may, without limitation, give an ailing kidney more blood flow, promote healing in an extremity, starve a growing tumor, or rest and heal the heart. The parameters of the circulation and perfusion enhancement system that determine the magnitude of the hemodynamic effects include, without limitation, its configuration (number and physical relationship of pumps and impellers), its location and orientation, its speed and power, the design of its flow and pressure modification elements, and its pattern of operation. Adjusting these parameters allows specification of desired combinations of effects useful for treating various diseases or conditions.

Figure 9:
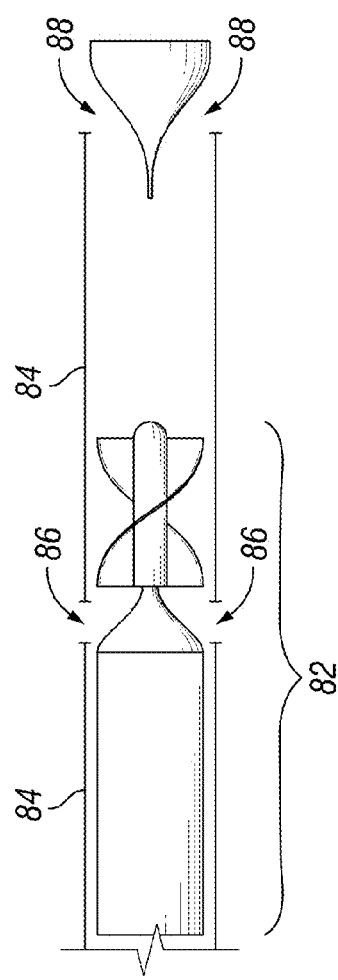
FIG. 9 is an illustrative embodiment of an intravascular pumping module.

In one embodiment (FIG. 9), a circulation and perfusion enhancement system comprises a pump (82) to accelerate fluid flow within a housing (84) with inlet ports (86) and outlet ports (88). This is the "push" configuration. Other embodiments may reverse the flow through the device described in FIG. 9 such that the ports (88) farther from the pump (82) are inlet ports and the ports (86) closer to the pump (82) are outlet ports. This is the "pull" configuration.

Figure 10:
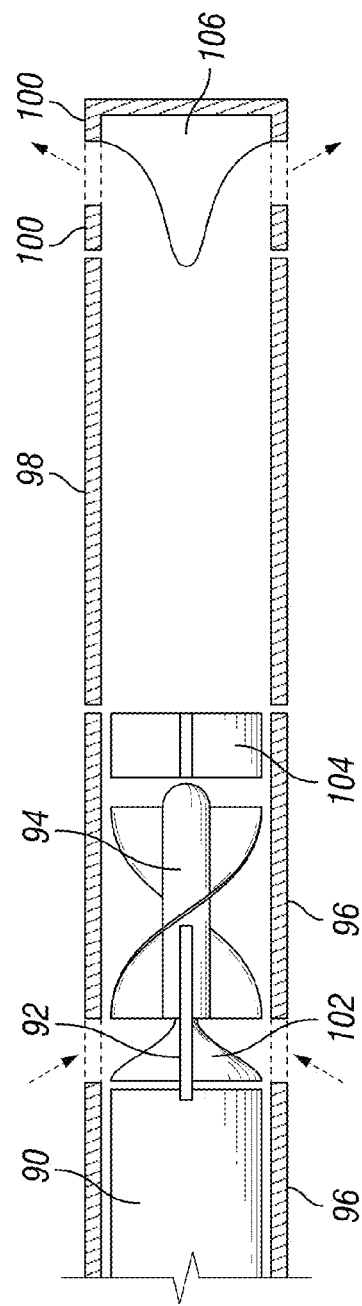
FIG. 10 is another illustrative embodiment of an intravascular pumping module.

FIG. 10 shows one embodiment of an intravascular pumping module, comprising a motor (90) driving a shaft (92) connected to an impeller (94). The impeller (94) lies inside the inlet housing (96) which is in turn connected to a flexible cannula (98) which is in turn connected to an outlet housing (100). The inlet housing (96) is connected to the motor (90). The inlet housing comprises an inlet flow director (102) and an intermediate flow director (104). The outlet housing comprises an outlet flow director or nozzle (106).

Figure 11:
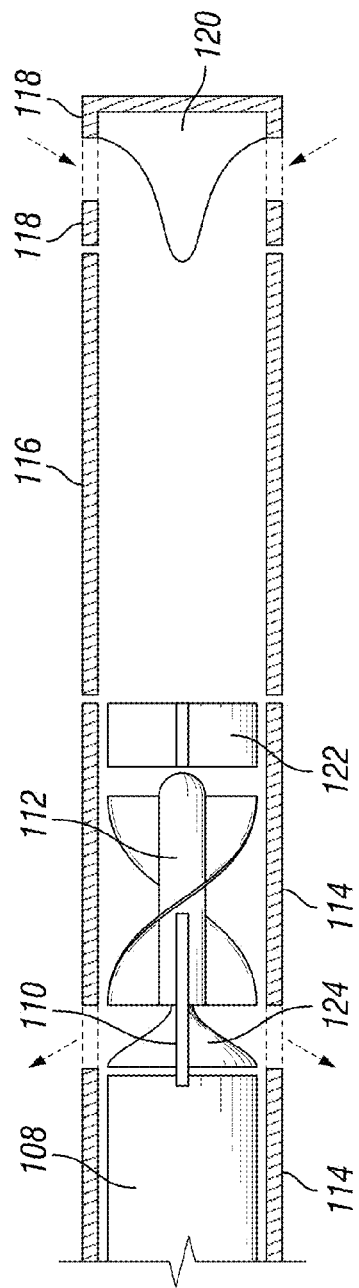
FIG. 11 is yet another illustrative embodiment of an intravascular pumping module.

FIG. 11 shows another embodiment of an intravascular pumping module, comprising a motor (108) driving a shaft (110) connected to an impeller (112). The impeller (112) lies inside the outlet housing (114) which is in turn connected to a flexible cannula (116) which is in turn connected to an inlet housing (118). The outlet housing (114) is connected to the motor (108). The inlet housing comprises an inlet flow director (120). The outlet housing comprises an intermediate flow director (122) and an outlet flow director or nozzle (124). This embodiment has very similar components and a reversed flow direction compared to the embodiment shown in FIG. 10.

As mentioned above, in embodiments with pumps with an impeller attached to the shaft of a rotary motor, a pump may be in the "push" or "pull" configuration. This is independent of whether the pump is pumping in or against the direction of native flow. In the push configuration, the motor is located at the inlet end of the pump, such that fluid entering the pump's inlet(s) moves past the motor to do so and fluid exiting the pump's outlet(s) is not obstructed by the motor. In the pull configuration, the motor is located at the outlet end of the pump, such that fluid entering the pump's inlet(s) is not obstructed by the motor and fluid exiting the pump's outlet(s) moves past the motor to do so. The selection of configuration may be important in various embodiments. For example, if the embodiment includes a cannula on the side of the impeller opposite the motor, fluid in that cannula will be at negative relative pressure if the pump is in the pull configuration and at positive relative pressure if the pump is the push configuration. Fluids like blood may behave differently (for example, in terms of hemolysis) when exposed to those different pressure environments.

Figure 1C:
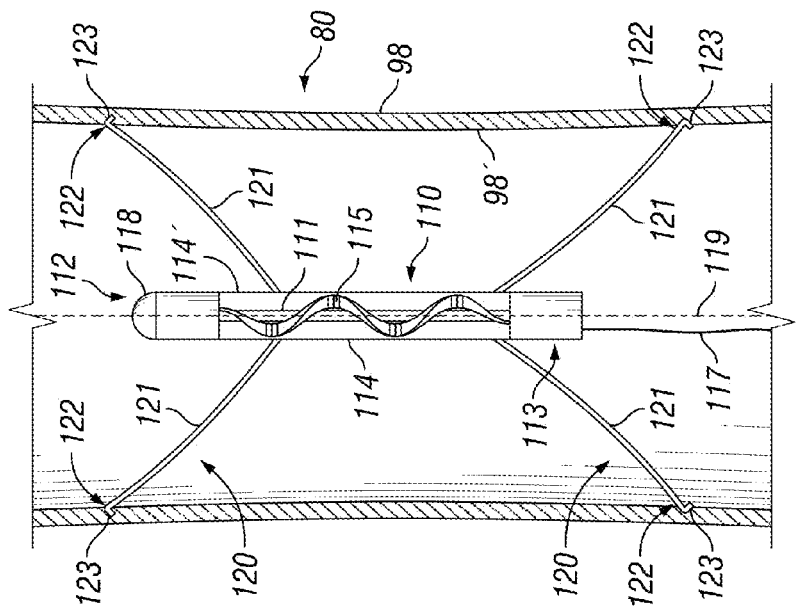
FIG. 1C is a partial cross-sectional view of intravascular pumping module in accordance with the present invention in a second deployed configuration.
Figure 1B:
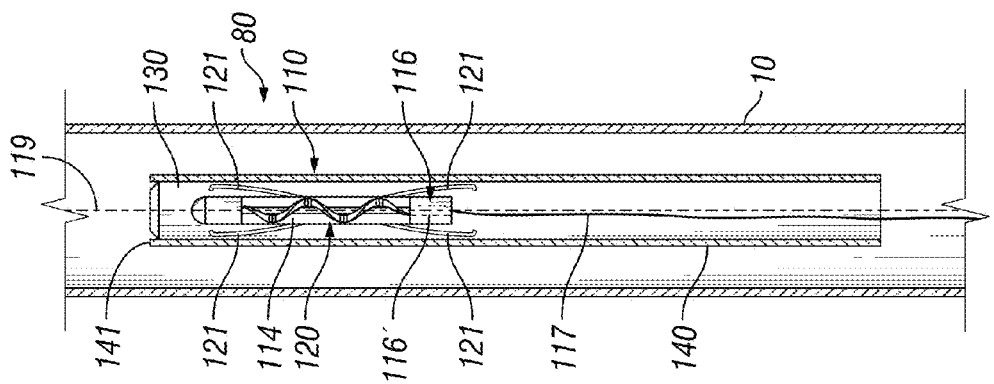
FIG. 1B is a partial cross-sectional view of the intravascular pumping module of the present invention in a first transluminal delivery configuration, the device being enlarged for clarity.

In some embodiments, the circulation and perfusion enhancement system is an intravascular blood pump that, together with the flow control elements, is delivered transluminally to the implantation site. For the purposes of illustration and clarity, the circulation and perfusion enhancement system is shown without flow control elements in FIG. 1C. The following nonlimiting example discusses placement of the circulation and perfusion enhancement system in the descending aorta. However, in other embodiments, placement can be in any accessible vessel or chamber of sufficient size. With reference to FIGS. 1B and 1C, in certain embodiments, the intravascular pumping module 80 of the present invention may include: a pump 110 which is percutaneously and transluminally delivered to a portion of the descending aorta 98 or other vessel or chamber (FIGS. 1A and 1C) of a patient 79 via the subclavian, iliac, or femoral artery 10 (FIG. 1B) of the patient 79; and a transluminally deliverable support structure 120 which secures, or anchors, pump 110 within the descending aorta 98 or other vessel or chamber. Intravascular pumping module 80 may be disposed within a portion of the descending aorta 98 or other vessel or chamber. In certain embodiments this disposition is preferably in a central portion of the descending aorta 98 or other vessel or chamber. Pump 110 pumps blood 81" drawing it downward from the ascending aorta 76, and discharging it further downward. Thereafter the oxygenated blood 81" from left ventricle 72 is circulated through the various arteries of the patient's body.

It should be apparent to one of ordinary skill in the art that other pumps 110, e.g. radial or displacement pumps, could be utilized in lieu of axial flow pump 111, provided pump 110 meets the required dimensions, may be used in a particular embodiment of the device, is bio-compatible and capable of operating in the environment of the body, specifically the aorta or other vessel or chamber, and able to pump blood. The pump or pumps in any particular embodiment may be driven electrically, pneumatically, mechanically or by any other method.

Still with reference to FIGS. 1B and 1C, in this embodiment pump 110 is a rotary pump and preferably is an axial flow pump 111 having first and second ends 112, 113, and pump 110 is preferably disposed within a housing 114. At least one spiral vane, or impeller, 115 is disposed within housing 114. Housing 114 may be approximately 18 French diameter in size, although other sizes may be selected. Pump 110 is preferably powered by a motor 116, such as an electric motor 116', which rotates impeller 115. Impeller 115 may be mounted on a shaft supported by bearings, or magnetically or hydrodynamically levitated, for rotation within housing 114. A power wire 117 is associated with motor 116, and as will hereinafter described in greater detail, it extends from intravascular pumping module 80 to a point at which it may be associated with a power source, such as a battery (not shown). Housing 114 may be provided with a top cover, or inflow cage, 118, which permits the passage of blood 81" into housing 114, as it is drawn into, pumped, or pulled into housing 114 by the rotation of impeller 115. Housing 114 is preferably made of a suitable metallic or plastic material, such as stainless steel, which is a bio-compatible material. Alternatively, other bio-compatible materials, including plastic materials, having the requisite strength and bio-compatibility characteristics which permit the desired use in a person's aorta or other vessel or chamber may be utilized.

Pump 110 may be powered by an implanted power device, or transformer, and may receive electric power from either an implanted power source or from a source of power located outside the patient's body 79. It should be readily apparent to one of ordinary skill that if desired other types of power could be utilized to power pump 110, such as hydraulic power or other types of power sources. The implanted power device, not shown, could be a conventional battery or a plutonium, or other nuclear material, power source.

In some embodiments, the diameter of the pump 110 will be less than the diameter of the vessel or chamber it is implanted in to provide a bypass region around the pump and move on without passing through the pump. Alternatively, fluids can recirculate through the pump one or more times by moving through the bypass region from the outlet of the pump to the inlet of the pump. The bypass region may be provided between pump housing and a wall surface of a vessel. For example, the embodiment shown in FIG. 1C provides a bypass region between pump housing 114 and wall surface 98' of aorta 98 or other vessel or chamber. Intravacsular pumping module 80 allows fluids to flow around or past the pump 80 through this bypass region. Further, when pump 110 is in operation, fluids may also flow into inlet 112 and out from outlet 113. Pump 110 and additional flow or pressure modification elements discussed herein may be designed to significantly impact the characteristics of this bypass flow.

In other embodiments, the diameter of the pump will occupy substantially the full diameter of the vessel or chamber the pump is implanted in. In these embodiments there will be essentially no bypass flow.

Figure 2A:
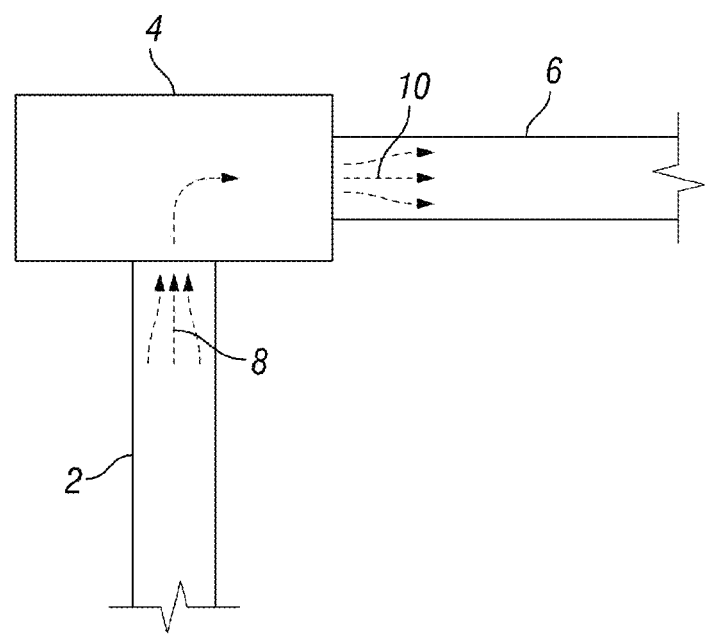
FIG. 2A shows a pump configuration.
Figure 2B:
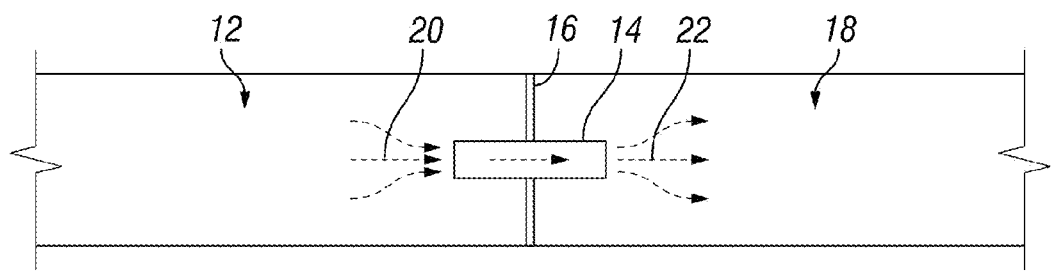
FIG. 2B shows an inline pump configuration.
Figure 4:
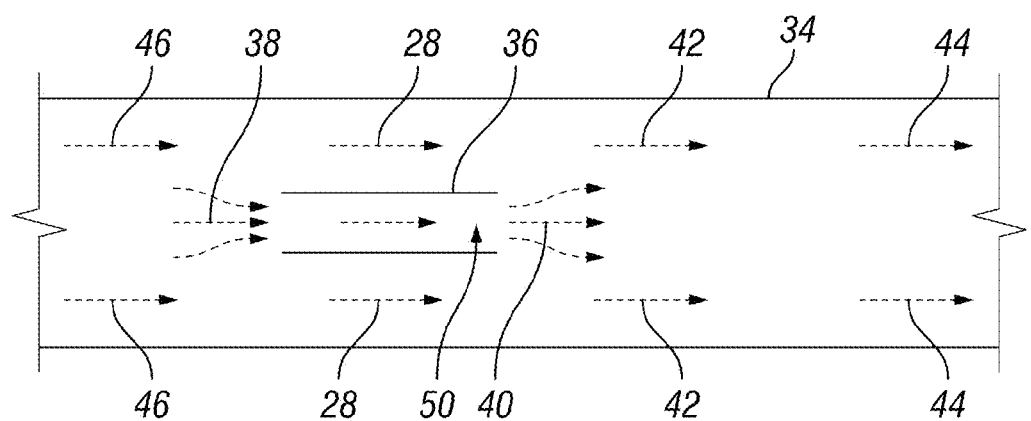
FIG. 4 is an illustrative embodiment of auto-entrainment.

A series flow pump with a bypass region (FIG. 4) has advantages over a partitioned inline pump (FIG. 2B). The lack of partition either simplifies configuration (since a partition is not required) or enables the pump to be placed in more locations (since no artificial barrier or natural partition like a heart valve or septum is necessary). The lack of provided partition in locations where no natural partition is present also reduces or eliminates the impedance to native flow. In cases where the pump fails, for example, the native flow is almost completely blocked in a partitioned inline pump whereas a failed pump in an auto-entrainment configuration provides a much less obstructed path for native flow. One advantage of series flow augmentation is the ability to augment flow in a vessel or chamber with no requirement to place a valve or add additional flow paths or make any changes to the vessel or chamber.

Still with reference to FIGS. 1B and 1C, support structure 120 of intravascular pumping module 80 includes a plurality of support members 121 associated with pump 110, which are may be associated with housing 114 or attached to any part of the system. Support members 121 may be secured to the outer surface, or outer wall surface 114', of housing 114 in any suitable manner, such as by welding or adhesive bonding. These struts may be located at any positions. Support structure 120 supports pump 110 within the descending aorta 98 or other vessel or chamber, in certain embodiments, preferably in a generally, centrally spaced relationship from the interior wall surface 98' of descending aorta 98 or other vessel or chamber. As will be hereinafter described in greater detail, support structure 120 anchors pump 110 within descending aorta 98 or other vessel or chamber for long or short term use to assist the pumping of blood 81" from ascending aorta 76 downwardly through descending aorta 98 or other vessel or chamber. At least two support members, or struts, 121 are disposed toward the upper end 112 of pump 110 and toward the lower end 113 of pump 110. Preferably, at least three support members, or struts 121, are substantially equidistantly disposed around each of the upper and lower ends 112, 113 of pump 110. Preferably, the support members 121 are formed of a suitable bio-compatible material, such as stainless steel or nitinol. Alternatively, other bio-compatible materials, including plastic materials, having the requisite strength, expansion or spring, and bio-compatible characteristics to function in the manner hereinafter described in a person's aorta or other vessel or chamber 98 may also be utilized.

Other devices and structures could be utilized for support structure 120, provided they permit the percutaneous transluminal delivery of the intravascular pumping module 80, and that after such delivery, the support structure 120 permits the disposition of the intravascular pumping module within the descending aorta or other vessel or chamber for long or short term use, as shown in FIG. 1C. By use of the terms "long term" and "long-term use", it is meant to be more than the relatively short period of time that conventional percutaneous left ventricular assist devices (LVADS) are used for (e.g. greater than 7-10 days, as previously described), and preferably on the order of at least a month and perhaps even a year or more. For example, a self-expanding stent 200, or stents, as are known in the art could be used for supportive structure 120, to support pump 110 in a substantially centrally spaced relationship from the interior wall surface 98' of aorta 98 or other vessel or chamber, as shown in FIGS. 1F and 1G. The stent, or stents, 200, schematically shown in FIGS. 1F and 1G, could have pump 110 centrally disposed therein with support members, or struts 121, being attached to the interior of the stent as shown in FIG. 1F.

As shown in FIG. 1B, the support structure 120, or plurality of support members 121 are disposed in a first configuration for percutaneous transluminal delivery to the desired portion of the descending aorta 98 or other vessel or chamber, as will be hereinafter described. In the first configuration, support members 121 are disposed substantially adjacent the outer wall surface 116 of housing 114, and are disposed substantially parallel to the longitudinal axis 119 of housing 114. In this first configuration, the overall diameter of pump 110, housing 114, and support structure 120 is reduced to permit the percutaneous transluminal delivery of the intravascular pumping module 80 through the femoral or iliac artery 10 of the patient to the desired location within the descending aorta 98 or other vessel or chamber or other vessel or chamber.

The support members, or struts 121, may be disposed in the pre-deployment configuration shown in FIG. 1B as by a sheath 130 or annular bands (not shown), which may be subsequently removed, or alternatively, the struts, or support members 121, when initially attached to the outer wall surface 114' of housing 114, have the disposition shown in FIG. 1B.

In this pre-deployment configuration, the support members, or struts 121, may be placed so that the struts fit into depressions or flexible areas in the motor or housing so as to minimize or eliminate any increase over the diameter of the housing. In such an embodiment, the hooks at the end of the struts, which might normally cause the biggest increase in diameter, could be place so they fit into the device ports in the pre-deployment configuration.

Upon the intravascular pumping module 80 being positioned within the desired portion of the descending aorta 98 or other vessel or chamber, the support members, or struts, 121, have a second, expanded configuration wherein the outer ends 122 of the support members 121 contact the inner wall surface 98' of descending aorta 98 or other vessel or chamber. The second disposition of the support members 121 shown in FIG. 1C may be achieved in a variety of ways. For example, the support members 121 may be formed as leaf springs, or spring members, wherein the support members 121 are biased to spring outwardly into the configuration shown in FIG. 1C. If support members 121 are in the form of leaf springs which bias outwardly toward descending aorta 98 or other vessel or chamber, they may be initially restrained into the configuration shown in FIG. 1B, by a sheath 130 or band-like member, as previously described, which may be removed when intravascular pumping module 80 has been delivered to its desired location within the descending aorta 98 or other vessel or chamber, whereby the support members, or struts, 121 would move outwardly into the configuration illustrated in FIG. 1C. Alternatively, support members 121 could be formed of a material, such as nitinol, whereby the support members 121 would initially have the configuration shown in FIG. 1B, and upon being heated by a resistive or inductive heater or by the blood flowing within aorta 98 or other vessel or chamber would spring outwardly into the configuration illustrated in FIG. 1C.

Alternatively, as shown in FIGS. 1F and 1G, the stent 200 with the pump, and struts disposed therein, could be compressed and disposed within a sheath 130 (as hereinafter discussed) and transluminally delivered as seen in FIGS. 1F and 1G, in a manner similar to and as shown as described with reference to FIG. 1B. Upon removal of sheath 130 the self-expanding stent 200 with pump 10 and struts 121 would expand outwardly as seen in FIG. 1G, similar to FIG. 1C, whereby the pump 110 would be supported in a generally centrally spaced relationship from the interior wall surface 98' of aorta 98 or other vessel or chamber.

Preferably, the intravascular pumping module 80 of the present invention is initially sheathed in a sheath 130 of approximately 21 French size in diameter in its undeployed configuration, as show in FIG. 1B, but other sizes are possible. The sheath size may be decreased in future embodiments of the system. If the struts 121 are of a spring-type design, the sheath 130 retains the support members 121 in the desired configuration illustrated in FIG. 1B. Housing 114 preferably has a diameter of approximately 18 French. The strut system, or struts 121, may also be deployed as a separate unit from the pump and initially deployed, and thereafter the pump 110 can then be deployed into the center of the strut system utilizing a locking mechanism, so that the pump may be removed and replaced at a later date so as to allow the ability to replace the pump if it should fail.

With reference to FIGS. 1B and 1C, preferably, the outer end 122 of at least one strut 121, and preferably each of the outer ends of the support members, or struts, 121 are provided with an anchor element, such as a small hook 123, or similar structure, which serves to anchor each of the struts 121 at the desired location within descending aorta 98 or other vessel or chamber. If desired, a plurality of anchor elements may be used.

The presence of the bypass region, or, in other words, the lack of a barrier or partition between the outlet and inlet of intravascular pumping module 80, creates a situation very different from traditional pumping. Systems and methods for increasing fluid flow and/or augmenting pressure and/or overcoming head in a tube, pipe, vessel, container, or reservoir typically depend on pumping across a partition separating the vessel or chamber into two or more volumes. These methods typically contain one source of fluid that is pumped from one volume to the other. In a discrete configuration (FIG. 2A) the two volumes (2 and 6) are separated by the pump itself. In an inline configuration (FIG. 2B), the pump is within the tube or vessel and the two volumes (12 and 18) are separated by a partition (16) within the tube or vessel. In either configuration, the separation of the two volumes prevents the increased flow and/or pressure at the pump outlet or discharge (10 and 22) from moving backwards and/or inducing flow toward the pump inlet flow or suction (8 or 20). In mechanical systems, the barrier (16) is usually a mechanical valve or barrier. In biological systems, the barrier (16) could be a biological or mechanical valve or barrier (e.g. a heart valve or septum or vessel wall).

Having an open bypass around the pump allows developed pressure or flow to "slip" back around the pump and recirculate, reducing the net work completed. While this possibility makes effective pumping more difficult and possibly less efficient in many cases, it also enables the opportunity to increase overall flow through entrainment.

Figure 3:
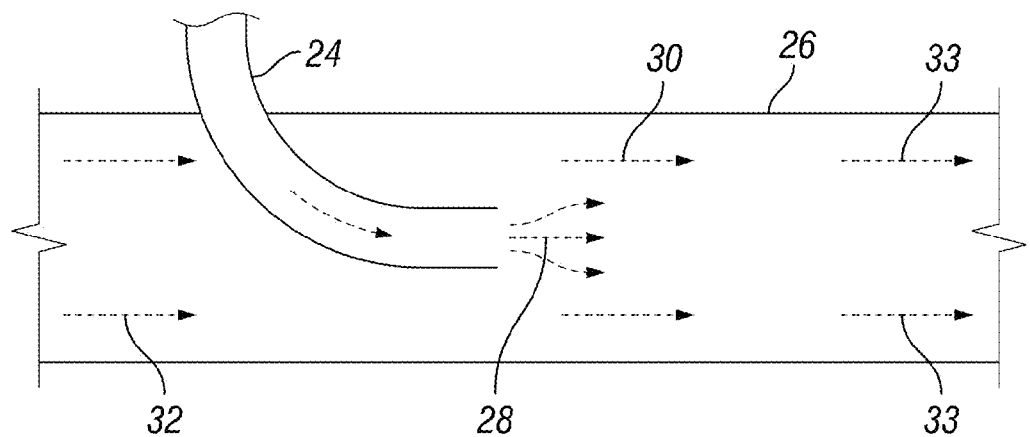
FIG. 3 is an illustrative embodiment of an entrainment method using a source/reservoir separated from upstream flow of a pump.

To understand the possibility the bypass path allows, consider an example from industry (this industrial example is not an embodiment of the present invention). Entrainment is often used industrially (in mining, for example). Entrainment methods (FIG. 3) use a jet of fluid (24) from a source or reservoir separate from or removed from or at a distance from the suction (or upstream flow) of the pump. This jet (24) may also be termed the motive flow. The motive flow or jet (24) exits and transfers momentum to the fluid (30) near the jet or present at that point in the vessel or tube (26). This momentum transfer accelerates the vessel fluid (30). The increased velocity of the vessel fluid (30) pulls the upstream fluid (32) along, accelerating the nearby fluid as well. This increase in vessel flow (30 and 32) by the motive flow (28) is called entrainment. In entrainment methods, total discharge or downstream flow (33) equals suction or upstream flow (32) plus motive flow (24).

Auto-entrainment (FIG. 4) describes the situation in which the flow (42 and 46) in a vessel or tube (34) is accelerated by a jet or motive flow (50) that is sourced from the suction or upstream vessel flow (46). This is entrained in a series flow modification system analogous in a nonlimiting way to the present invention. The motive flow (50) is formed by vessel flow that enters as a pump inlet flow (38), is accelerated by a pump (36), and exits as a pump outlet flow (40). The portion of the upstream flow (46) that does not flow through the pump (36) is termed bypass flow (48). In auto-entrainment, total discharge or downstream flow (44) equals suction or upstream flow (46) equals motive flow (50) plus bypass flow (48). This differs from entrainment, where the bypass flow equals the suction flow and the motive flow is sourced separately. Effective auto-entrainment may increase flow above what the pump alone can achieve.

In entrainment and auto-entrainment, the native flow can be described as the flow (equal to the upstream flow and the downstream flow) present with no increase due to the motive flow. For the entrainment configuration shown in FIG. 3, the native flow is equal to the upstream flow (32) and equal to the downstream flow (33) when the motive flow (24) is zero. For the auto-entrainment configuration shown in FIG. 4, the native flow is equal to the upstream flow (46) and equal to the downstream flow (44) when zero power is supplied to pump (36). Some small motive flow (50) may be present simply due to a portion of the upstream flow (46) moving passively through the pump (36).

Figure 5:
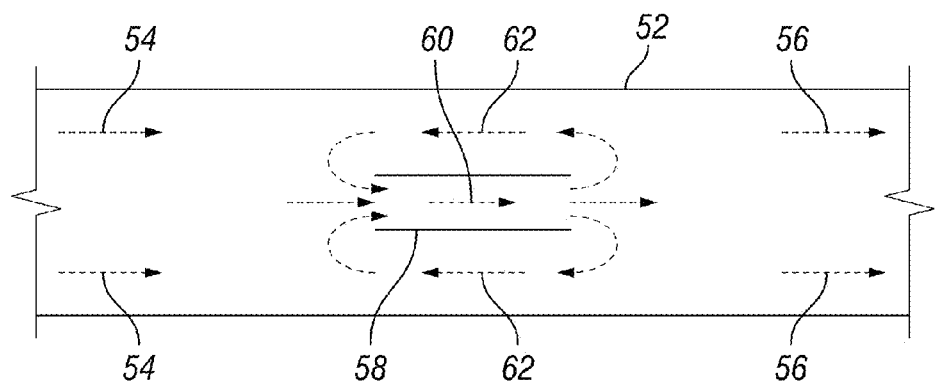
FIG. 5 is an illustrative embodiment of reverse bypass flow.

In auto-entrainment, recirculation is possible under certain circumstances (FIG. 5). In this case, the bypass flow (62) moves in the opposite direction of the upstream flow (54), downstream flow (56), and motive flow (60) through the pump (58). As when the bypass flow is in the same direction as the upstream and downstream flows, total downstream flow (56) equals upstream flow (54) equals motive flow (60) plus bypass flow (62). Total flow (equal to suction or upstream flow equal to discharge or downstream flow) may still be increased above native flow alone in auto-auto-entrainment with reverse bypass flow.

The following paragraphs discuss the flow and pressure modification elements and how they can be adjusted.

The configuration of the inlet of the device may be adjusted in a number of ways to minimize reverse bypass flow, maximize efficiency, maximize auto-entrainment and total flow, or alter other parameters of performance. Among other parameters, the overall shape of the inlet end of the device as well as the size, number, shape, and location of inlet ports may be varied.

Figure 14A:
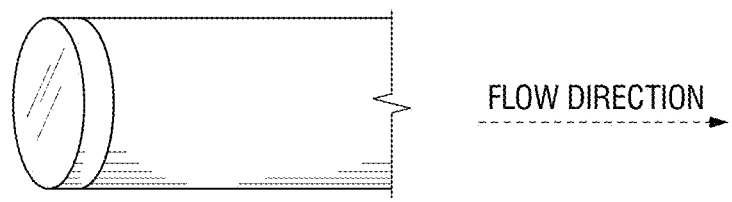
FIGS. 14a-14c are illustrative embodiments of flat (a), conical (b), and ellipsoid shaped (c) nose cones.
Figure 14B:
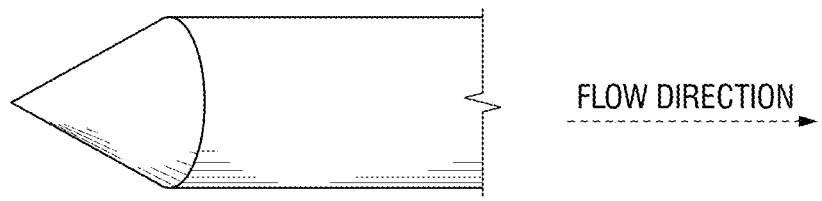
Figure 14C:
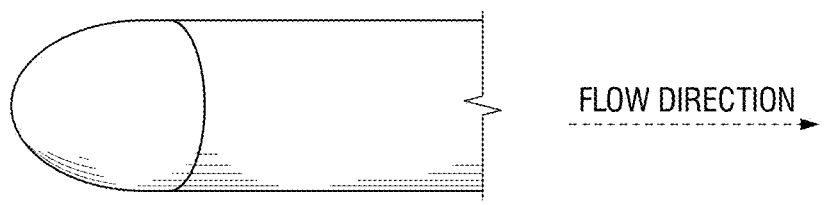

The inlet end of the device may comprise a "nose cone" of an arbitrary shape to modify the suction flow around and into the device. FIG. 14 shows (a) flat, (b) conical, and (c) ellipsoid shaped nose cones as examples.

Figure 15:
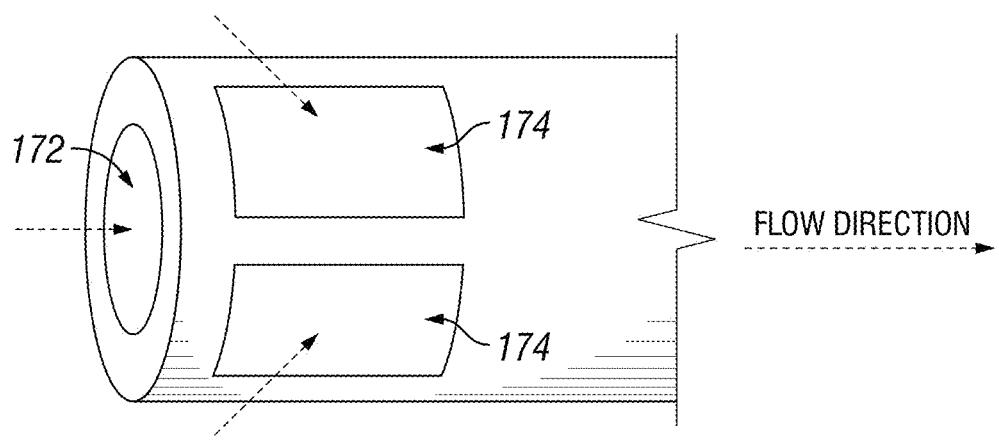
FIG. 15 is an illustrative embodiment of inlet flow.
Figure 16A:
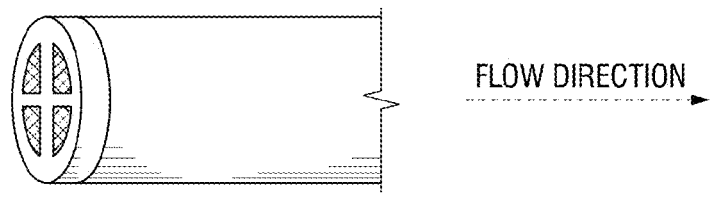
FIGS. 16a-16d are illustrative embodiments of a flat nose cone with axial ports (a), a flat nose cone with radial ports (b), an ellipsoid nose cone with axial ports (c), and an ellipsoid nose cone with radial ports (d)
Figure 16B:
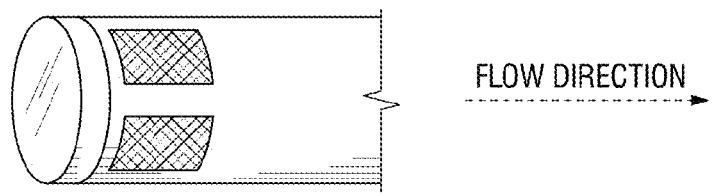
Figure 16C:
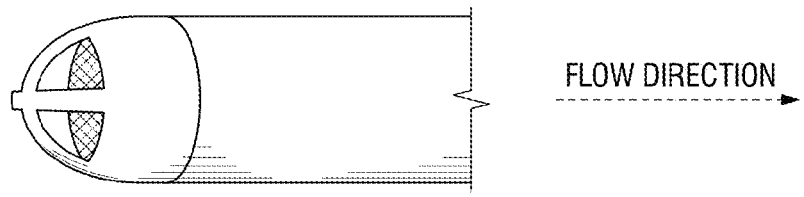
Figure 16D:
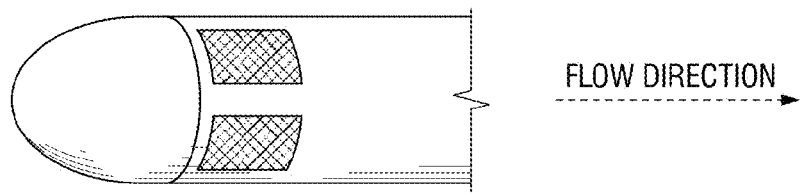
Figure 17:
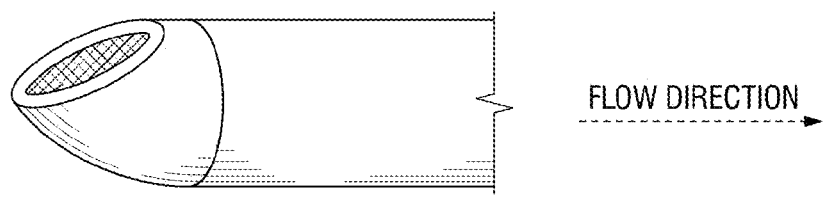
FIG. 17 is an illustrative embodiment of a non-symmetric, hybrid inlet.
Figure 18A:
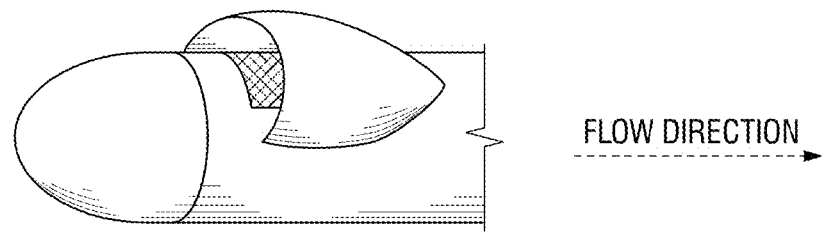
FIGS. 18a-18d are illustrative embodiments of axial inlet ports (b) and radial inlet ports (a, c) and non-symmetric inlet ports (d)
Figure 18B:
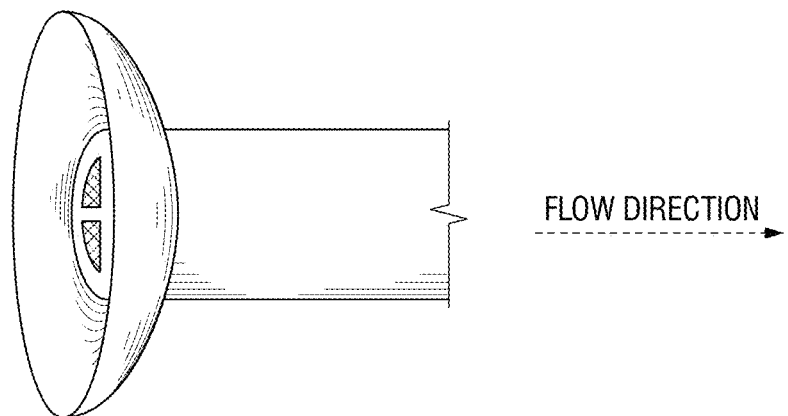
Figure 18C:
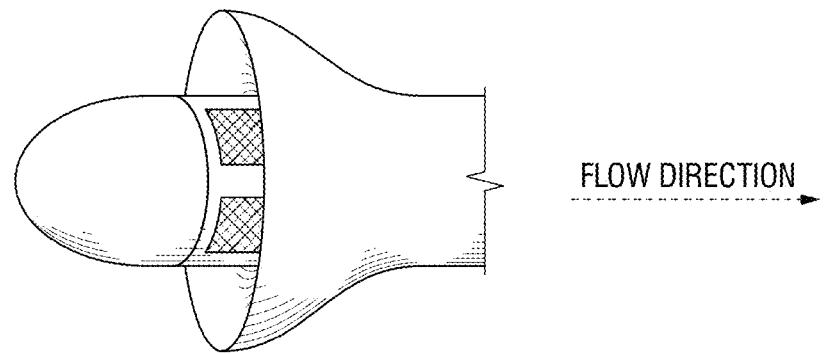
Figure 18D:
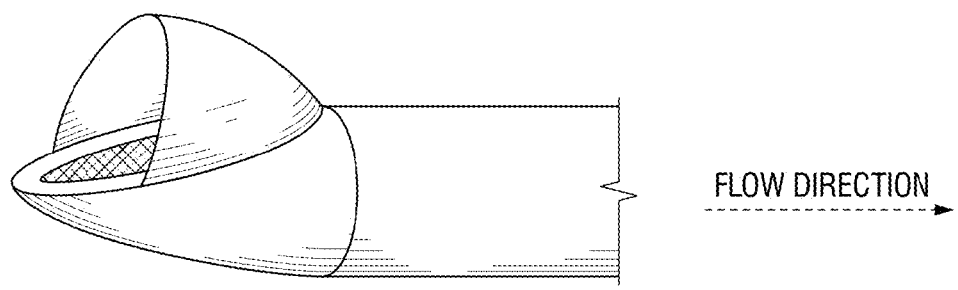

As shown in FIG. 15, the basic inlet flow may be through any combination of axial ports (172) (at the inlet end of the device) and radial ports (174) (on the side of the device). The inlet flow through both axial and radial inlet ports may be adjusted by adjusting the size, number, and location of the ports. FIG. 16 shows examples for a flat nose cone with axial ports (a), a flat nose cone with radial ports (b), an ellipsoid nose cone with axial ports (c), and an ellipsoid nose cone with radial ports (d). Many other combinations of these configurations are possible. FIG. 17 shows a non-symmetric, hybrid example in which inlet flow enters through one side of the nose cone. Such non-symmetric inlet port design may be useful in cases where the device sits in proximity to the wall of the vessel or tube or reservoir.

The inlet end of the device may also comprise geometries or shapes, or inlet flow receptors (FIG. 17w-z), one purpose of which may be to enhance flow into the inlet ports. In one embodiment, one or more inlet flow receptor (FIG. 17w-z) may be provided near the inlet port to increase flow to the inlet port. The shapes utilized for inlet flow receptor may increase flow through the inlet ports by increasing the cross-sectional area of the device and directing the flow impacting such incremental cross-sectional area into the inlet ports. Such shapes may also impact the overall efficiency and effectiveness of the device by altering suction or bypass flows or pressures. FIG. 18 shows examples for axial inlet ports (b) and radial inlet ports (a, c) and non-symmetric inlet ports (d). Shapes like those shown in FIG. 18 may also serve to prevent the axial inlet port from coming too close to or in contact with the wall of the vessel or tube or reservoir. This may be helpful in cases where the vessel wall is flexible or in cases where the device has a relative wide range of motion within the vessel or tube or reservoir.

The configuration of the outlet of the device may be adjusted in a number of ways to minimize reverse bypass flow, maximize efficiency, maximize auto-entrainment and total flow, or alter other parameters of performance. Among other parameters, the overall shape of the outlet end of the device as well as the size, number, shape, and location of outlet ports may be varied.

Figure 19A:
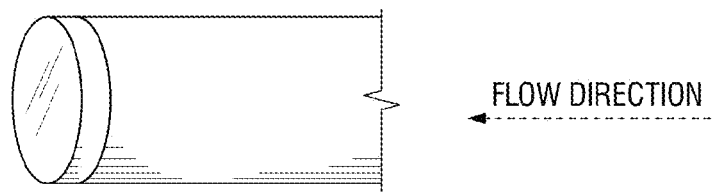
FIGS. 19a-19c are illustrative embodiments of flat (a), conical (b), and ellipsoid shaped (c) tail cones.
Figure 19B:
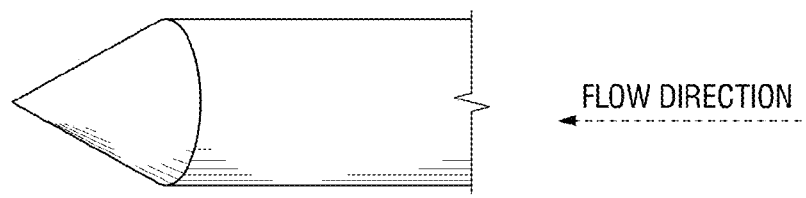
Figure 19C:
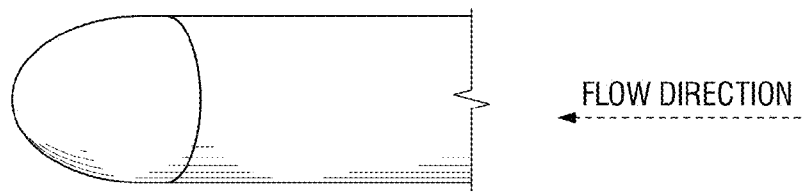

The outlet end of the device may comprise a "tail cone" of an arbitrary shape to modify the discharge flow path out of and around the tail end of the device. FIG. 19 shows (a) flat, (b) conical, and (c) ellipsoid shaped tail cones as examples.

Figure 20:
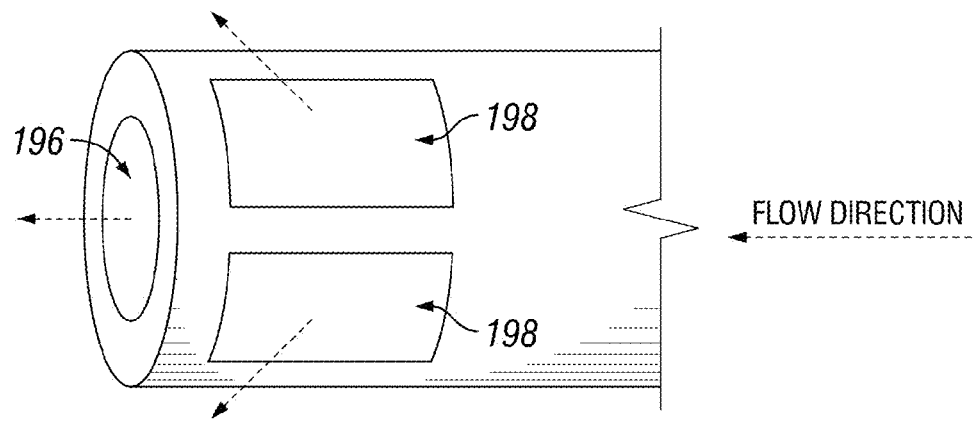
FIG. 20 is an illustrative embodiment of outlet flow.
Figure 21A:
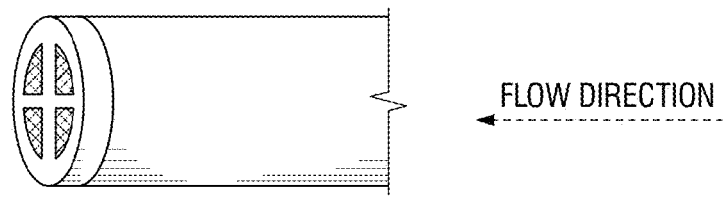
FIGS. 21a-21d are illustrative embodiments of a flat tail cone with axial ports (a), a flat tail cone with radial ports (b), an ellipsoid tail cone with axial ports (c), and an ellipsoid tail cone with radial ports (d)
Figure 21B:
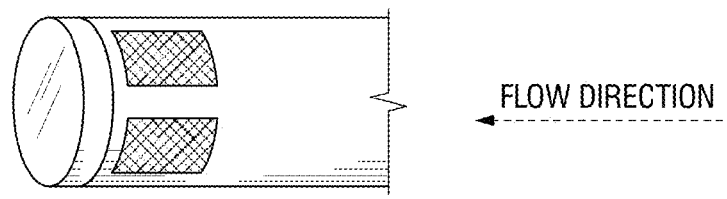
Figure 21C:
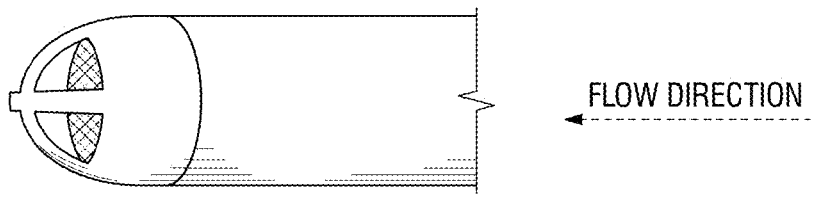
Figure 21D:
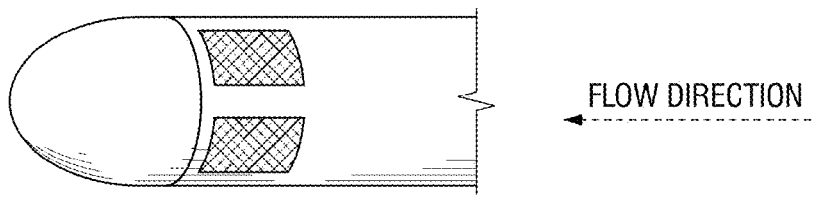
Figure 22:
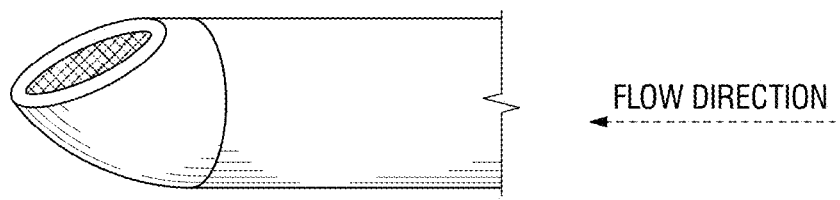
FIG. 22 is an illustrative embodiment of a non-symmetric, hybrid outlet.
Figure 23A:
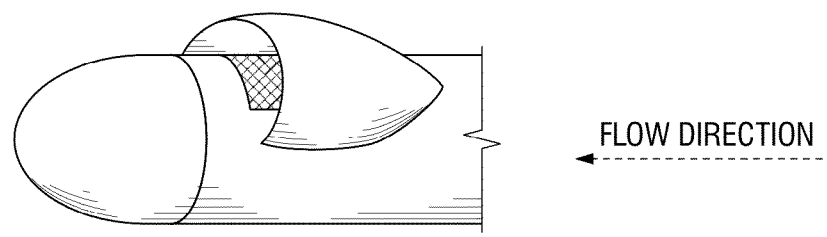
FIGS. 23a-23d are illustrative embodiments of axial outlet ports (b) and radial outlet ports (a, c) and non-symmetric outlet ports (d)
Figure 23B:
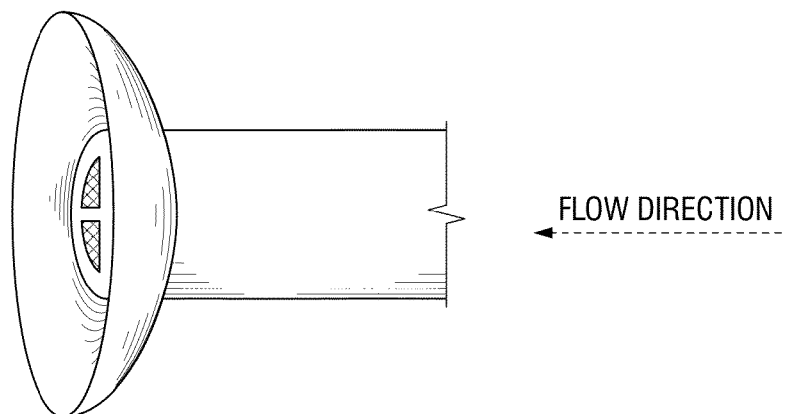
Figure 23C:
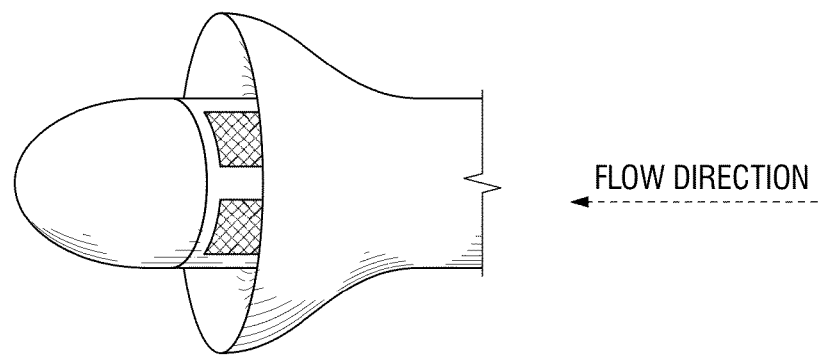
Figure 23D:
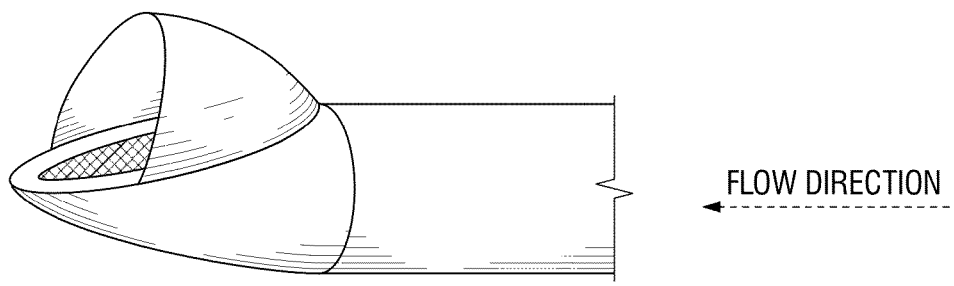

As shown in FIG. 20, the basic outlet flow may be through any combination of axial ports (196) (at the outlet end of the device) and radial ports (198) (on the side of the device). The outlet flow through both axial and radial outlet ports may be adjusted by adjusting the size, number, and location of the ports. FIG. 21 shows examples for a flat tail cone with axial ports (a), a flat tail cone with radial ports (b), an ellipsoid tail cone with axial ports (c), and an ellipsoid tail cone with radial ports (d). Many other combinations of these configurations are possible. FIG. 22 shows a non-symmetric, hybrid example in which outlet flow exits through one side of the tail cone. Such non-symmetric outlet port design may be useful in cases where the device sits in proximity to the wall of the vessel or tube or reservoir.

The outlet end of the device may also comprise geometries or shapes, or outlet flow enhancers (FIG. 23h-k), one purpose of which is to enhance flow out of the outlet ports. In one embodiment, one or more outlet flow enhancers (FIG. 23h-k) may be provided near the outlet port to increase flow to the outlet port. The shapes utilized for outlet flow enhancers may enhance or modify flow through the outlet ports or the pressure profile of such flows by modifying the path or pressure profile of the bypass flow and changing how the outlet flow and the bypass flow interact. Further, the outlet flow enhancers may also be shaped to minimized reverse bypass flow. FIG. 23 shows examples for axial outlet ports (b) and radial outlet ports (a, c) and non-symmetric outlet ports (d).

Figure 24A:
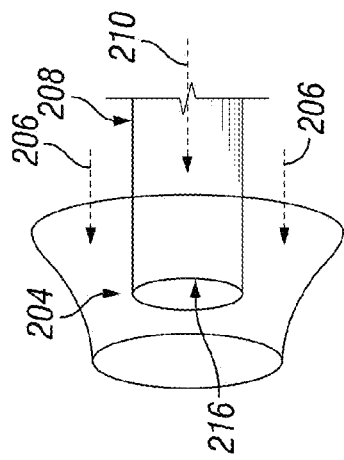
Figure 24B:
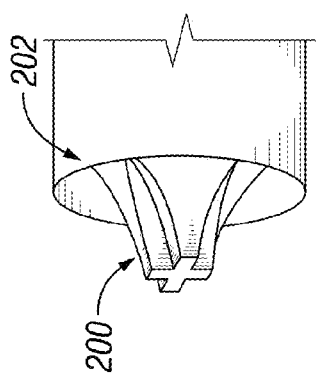
Figure 24C:
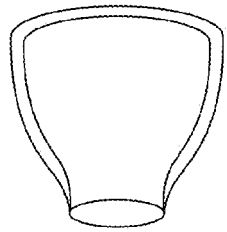
Figure 24D:
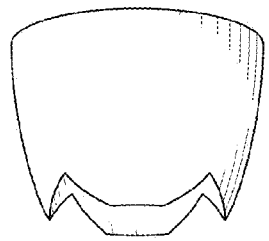
Figure 24E:
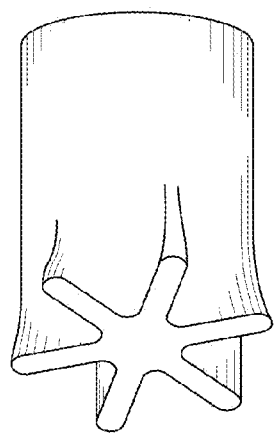
Figure 24F:
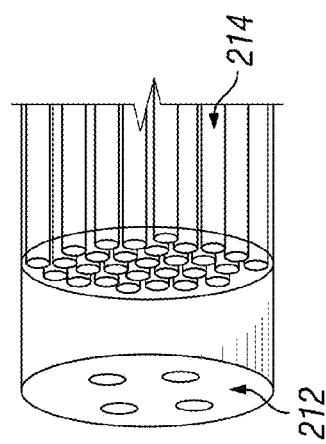
Figures 1, 24G:
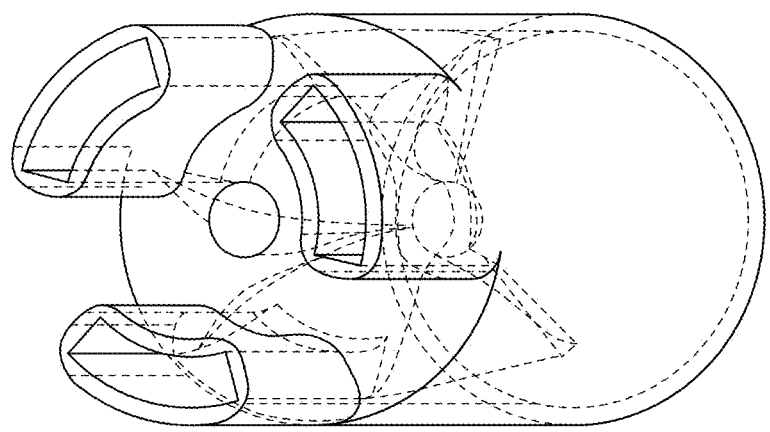
Figures 2, 24G:
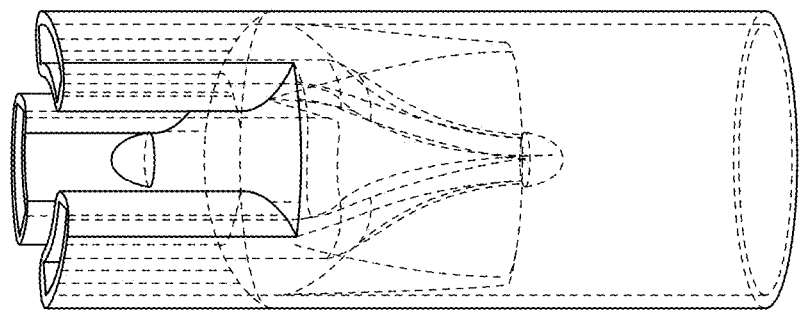
Figure 24H:
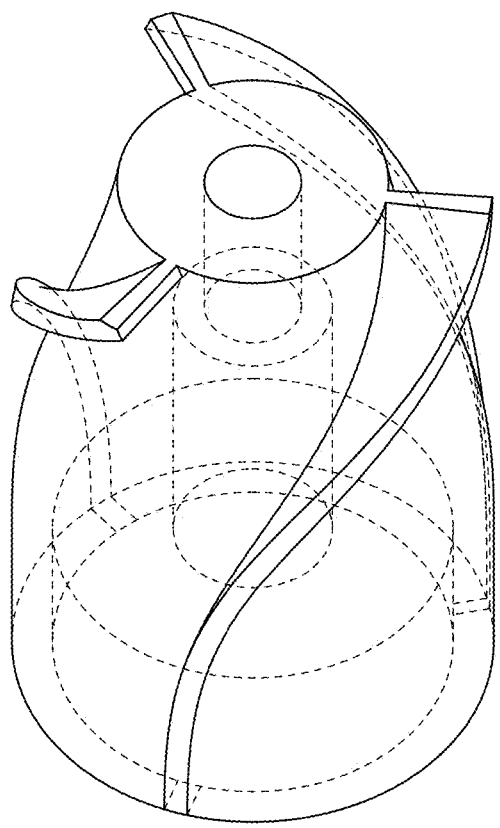
Figure 24I:
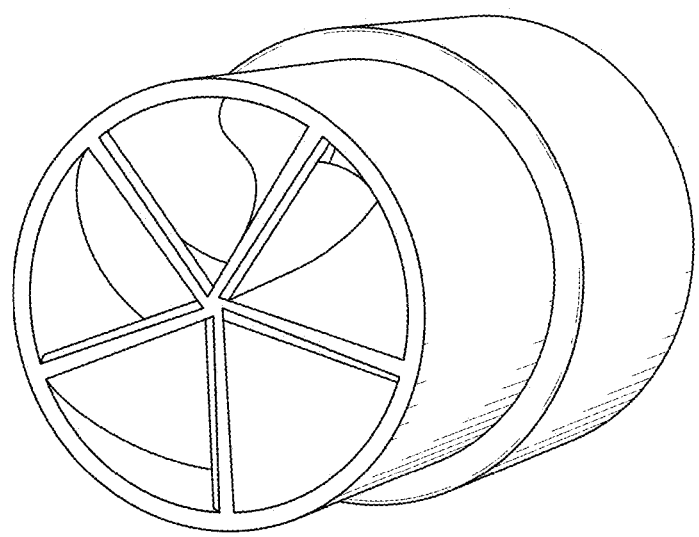

The outlet design for axial outlet ports or radial outlet ports may comprise an outlet nozzle of any shape known in the art of jet nozzle design. Such nozzles may be designed to enhance certain flow characteristics including, but not limited to, any combination of turbulence, swirl, or particular velocity components. FIGS. 24A-I shows several examples for axial outlet ports with nozzles. FIG. 24a shows a convergent nozzle. FIG. 24b shows a spike nozzle with a flow element (200) protruding from the outlet housing (202). FIG. 24c shows a bypass flow mixing nozzle. The shroud (204) captures and directs a portion of the bypass flow (206) toward the outlet port (216) of the outlet housing (208), enhancing the mixing of the bypass flow (206) and the outlet flow (or motive flow) (210) and thereby altering the interaction of the outlet flow and the bypass flow and the resultant flow and pressure profiles. FIG. 24d shows a laminar flow nozzle comprising a flow straightener (214) and an outlet orifice plate (212). The outlet orifice plate (212) may have any number of outlet ports of any shape. The flow straightener (214) may comprise elements that serve to enhance swirl or add skew components to the outlet velocity. FIG. 24e and FIG. 24f each show an example of an indeterminate origin (or IO) nozzle. FIGS. 24g-1 and 24g-2 shows two views of an inducement nozzle that draws the native flow into the center of the lumen, surrounded by outlet jets. FIG. 24h shows a swirl reducing flow straightener. FIG. 24i shows a swirl reducing straightening nozzle. In any of these embodiments, the goal may be to adjust or modify the width, angle, shape, swirl, turbulence, or other attributes of the outlet jet or its mixing with the bypass flow, independently or in combination. Radial outlet ports may also comprise nozzles of any arbitrary type. Elements like diffusers or porous media with certain characteristics may also be used to condition flow and pressure upstream or downstream of the nozzle.

Embodiments designed for enhancing circulation or perfusion may also use nozzles as discussed in connection with FIGS. 24A-I to alter or augment or enhance or control the flow and pressure changes created by the device.

Figure 33:
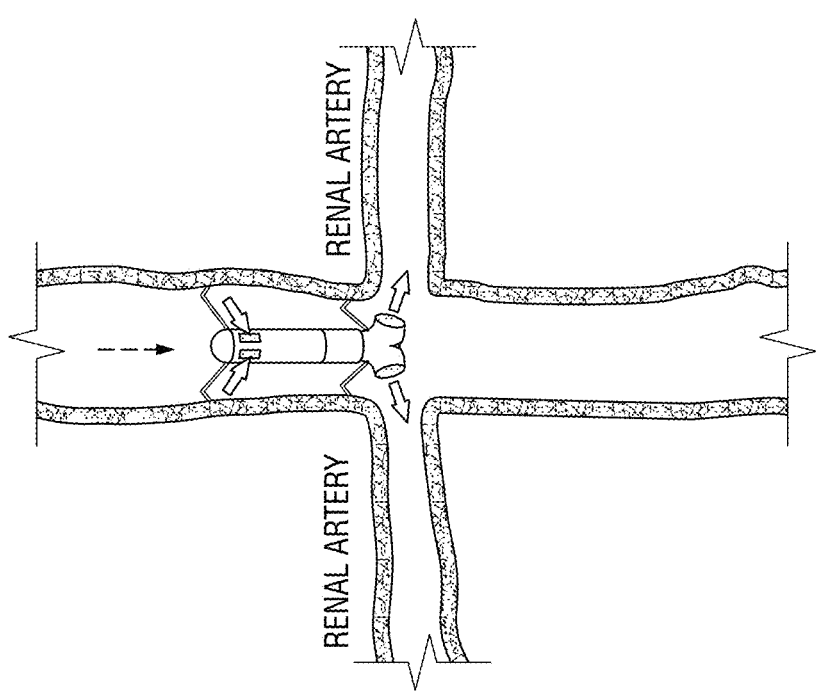
FIG. 33 shows configuration of outlet ports to selectively enhance kidney perfusion.

In one set of embodiments (illustrated in FIG. 33), the configuration of outlet flow ports is adjusted to enhance kidney perfusion by selectively increasing flow and pressure to the renal arteries.

Various nozzle designs shown in the figures generate confined, laminar flow.

Outlets promoting/reducing swirl may be provided.

In certain embodiments, the device may contain one or more flow directors that serve to modify the direction or velocity or other parameter of the motive flow as it enters the device, travels through the device, or exits the device. FIGS. 25a-25g shows several examples of such flow directors. Flow directors that modify flow into (e.g., FIG. 10 (102)) or out of (e.g., FIG. 10 (106)) the device may be referred to as "flow-around" flow directors and flow directors that modify flow through the device (e.g., FIG. 10 (104)) may be referred to as "flow-through" flow directors.

FIG. 25a shows a flow-around flow director (188) as an element of the inlet housing (190). FIG. 25b shows a flow-around flow director (192) as an element of the outlet housing (194). A flow-around flow director may have any arbitrary shape. FIG. 25c shows a flow-around flow director that is a solid of revolution.

Flow directors may comprise elements that serve to modify selective components of the motive flow. For example, flow directors may have vanes to reduce or eliminate radial components of motive flow velocity. In other embodiments, the vanes may be formed into a spiral or corkscrew shape in order to impart radial components to the motive flow velocity. FIGS. 25d-1 and 25d-2 shows two views of a flow-around flow director with a two vanes (218) built into the solid of revolution (220). FIG. 25e shows a flow-around flow director with four vanes (222) built into the solid of revolution (224). In general, a flow director may have any number of vanes with regular or irregular spacing between those vanes.

FIG. 25f shows a four vane flow-through flow director. FIG. 25g shows a three vane flow-through flow director. In general, a flow director may have any number of vanes with regular or irregular spacing between those vanes. A flow-through flow director may also comprise elements creating any number of distinct flow paths that remain independent or interconnect with one another. The flow straightener (214) shown in FIG. 24d is an example of such a flow-through flow director comprising elements creating a large number of independent distinct flow paths. These flow paths may be designed to adjust, modify, augment, change, impart, enhance, reduce, or eliminate certain axial or radial or skew velocity components of the motive flow.

Flow directors may also have some characteristics of jet nozzles including, but not limited to, diameters that vary with longitudinal distance (e.g. convergent or divergent sections) or sections with indeterminate origin or irregular circumferences.

In some embodiments, the struts or other support mechanisms may also serve to direct, restrict, block, occlude, and/or otherwise modify the bypass flow and may have special shapes or features for that purpose.

Any flow director that extends beyond the basic diameter or length of the device can have pre-and post-deployment configurations. Deployment can be due to spring constant or shape memory with heat or current. One nonlimiting example of this is a one-way valve designed to prevent recirculation through the bypass region and described relative to the intravascular pumping module for simplicity.

Figure 1D:
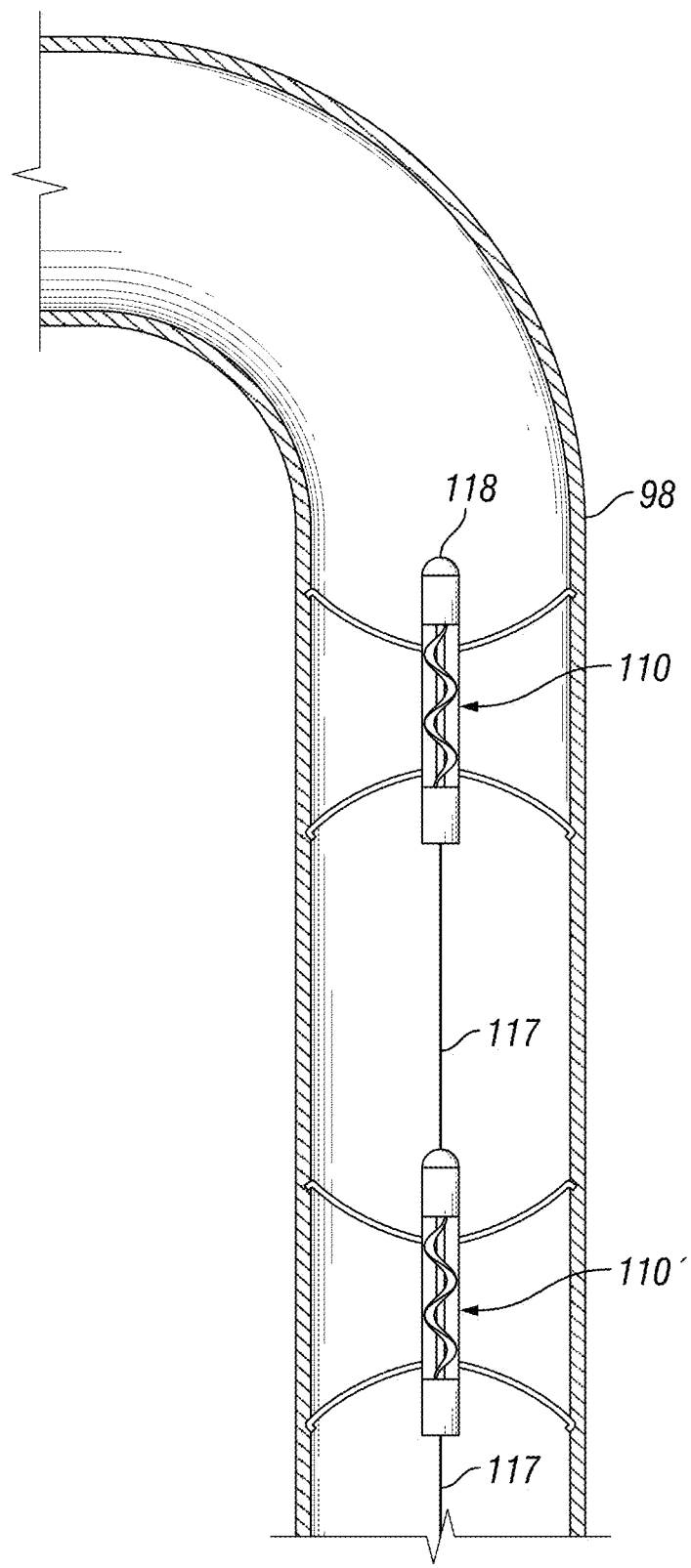
FIG. 1D is a partial cross-sectional view of another embodiment of the intravascular pumping module in accordance with the present invention in a second deployed configuration.
Figure 1E:
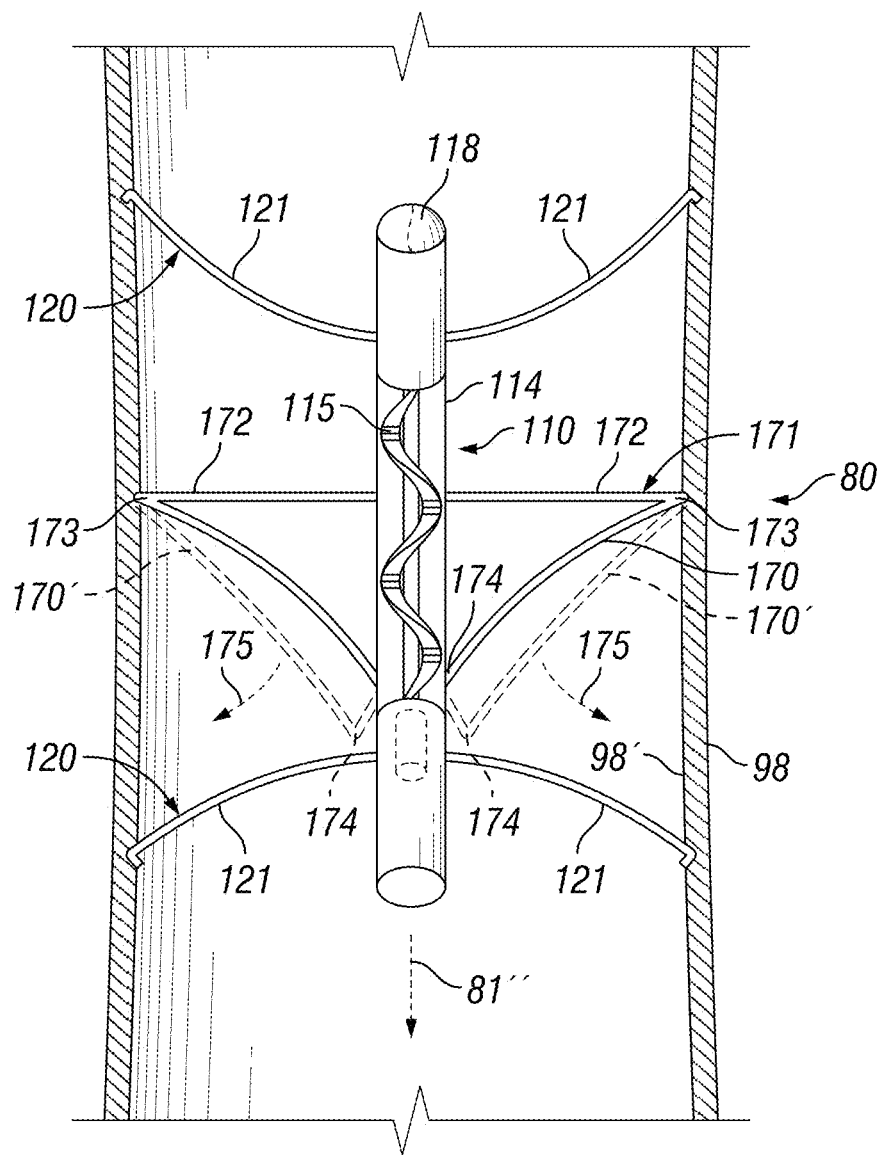
FIG. 1E is a partial cross-sectional view of an embodiment of the intravascular pumping module in accordance with the present invention including a one-way valve.

With reference to FIG. 1E, a figure similar to FIG. 1C, the intravascular pumping module 80 is provided with a one-way valve 170, and is shown disposed in the descending aorta 98 or other vessel or chamber. The same reference numerals are used for the same components shown and described in connection with FIGS. 1B and 1C. One-way valve 170 may be provided to prevent backflow of blood 81" from flowing upwardly through the bypass region back into descending aorta 98 or other vessel or chamber. One-way valve 170 may be provided in any suitable manner, such as by supporting one-way valve 170 by a strut system 171 associated with housing 114. Strut system 171 may include a plurality of strut members 172 which may be deployed in a similar manner to strut members 121 of strut system 120 to bring the circumferential end, or lip, 172 of one-way valve 170 into a sealing relationship with the interior surface 98' of descending aorta 98 or other vessel or chamber or other vessel or chamber. The other, smaller diameter circumferential end, or lip, 174 of one-way valve 170 is shown in FIG. 1E disposed in its sealed relationship with respect to housing 114, whereby backflow of blood 81" upwardly into descending aorta 98 or other vessel or chamber is prevented. As blood 81" is pumped to flow downwardly into descending aorta 98 or other vessel or chamber, one-way valve 170 may open as shown by dotted lines 170', whereby one-way valve 170 opens as shown in the direction of arrows 175, whereby the circumferential lip 174 of one-way valve 170 moves outwardly from housing 114 to permit blood 81" to flow not only through pump 110, but also through bypass region in the normal direction of native flow and into descending aorta 98 or other vessel or chamber.

One-way valve 170 may be made of any suitable biocompatible, or biomaterial, including plastic materials, having the requisite strength and bio-compatibility characteristics which permit the desired use in a person's aorta or other vessel or chamber and permits the function of one-way valve 170. Rigid biomaterials or flexible biomaterials may be utilized for the construction of one-way valve 170.

In addition to the design and location of the inlets, outlets, and flow directors, several physical dimensions (FIG. 7) of the pump can be varied to minimize reverse bypass flow, maximize efficiency, or maximize auto-entrainment and total flow. The overall length (68) between inlet ports (64) and outlet ports (66) of the pump can be changed. Longer lengths (68) provide for a higher bypass volume with more kinetic energy contained in the bypass flow (126) making it more difficult to reverse flow direction. Longer lengths (68) also cause more resistance to the bypass flow (126), reducing its energy and making it easier to reverse flow direction. Whether the net effect is to make reverse bypass flow more or less likely depends on the specific fluid in question and the specific geometry of the bypass path. The specific geometry of the bypass path, or the fluid pathway bypassing the pump (128), depends on the height (72) of the bypass path and the position or orientation or configuration of the pump (128) within the tube or vessel (130) as discussed in connection with FIG. 6 below. The bypass height (the thickness of the bypass annulus) is the diameter of the vessel (130) minus the diameter (70) of the pump (128).

Adjusting Physical Dimensions: All the physical dimensions of the device may be varied to enhance or modify or target or limit or control pressure and flow in the region of the pump. The description above in connection with FIG. 7 discusses many of these physical dimensions or parameters.

Figure 7:
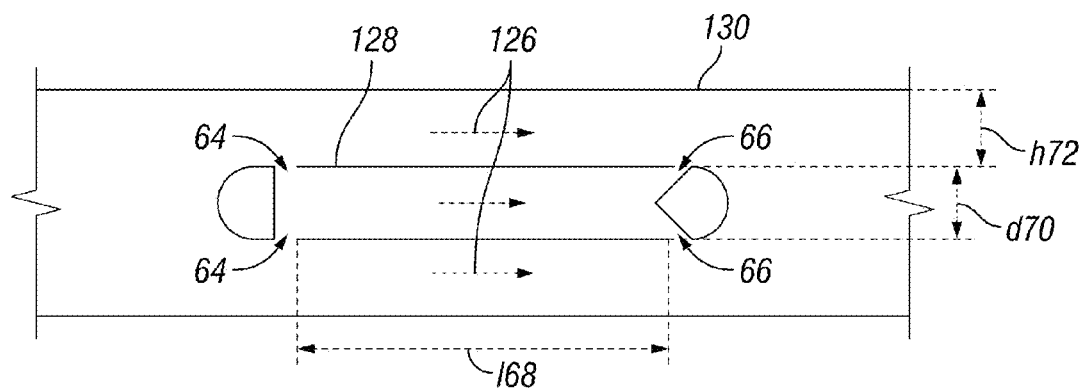
FIG. 7 is an illustrative embodiment of an intravascular pumping module configured to minimize reverse bypass flow.

Referring to FIG. 7, the overall length (68) between inlet ports (64) and outlet ports (66) of the pump can be adjusted to differentially augment flow to vessels up and downstream of the renal arteries. The diameter (70) of the device (128) can also be varied to affect bypass flow (126) and the flow and pressure profiles around the pump. The diameter (70) of the device (128) may also be made to vary along the length of the device such that the device has an arbitrary profile. In certain embodiments, the diameter of some part of the device may be large enough to effectively reduce or minimize bypass flow in the vessel the device sits in. This may be due to the minimum required diameter of the device in smaller vessels or due to a portion of the device designed to have a large diameter in larger vessels.

In embodiments where the device sits against vessel wall, the shape of the device may not be symmetric around the longitudinal axis of the device. For example, one portion of the device may be shaped to fit against the vessel wall while the portion of the device away from the wall of the vessel may have an arbitrary shape.

In embodiments with more than one pump or cannula or inlet or outlet, the size and shape of each segment or component or part or aspect of the device can be individually varied or adjusted.

Figure 6A:
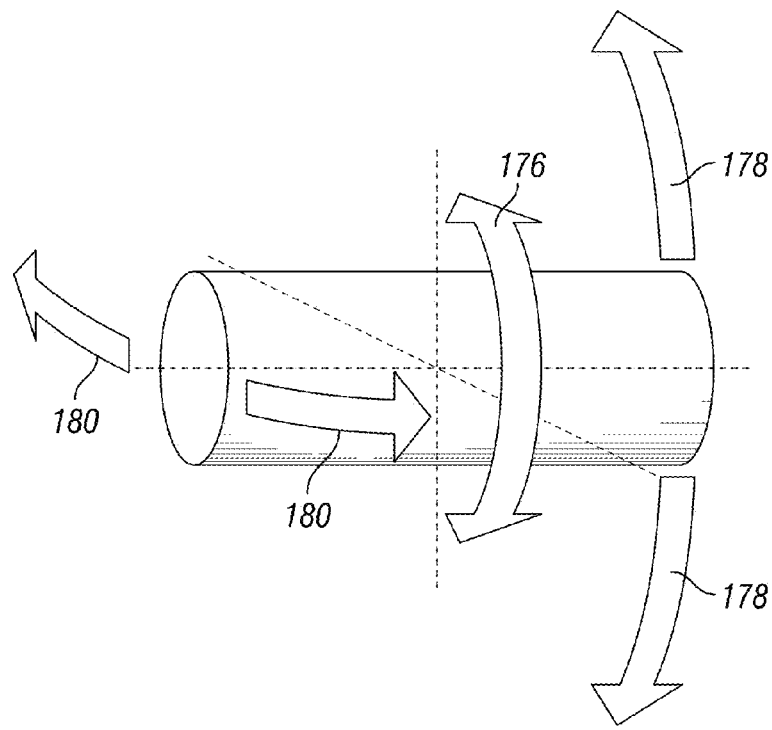
FIGS. 6a and 6b are illustrative embodiments of position, orientation, and configuration of an intravascular pumping module in a vessel.
Figure 6B:
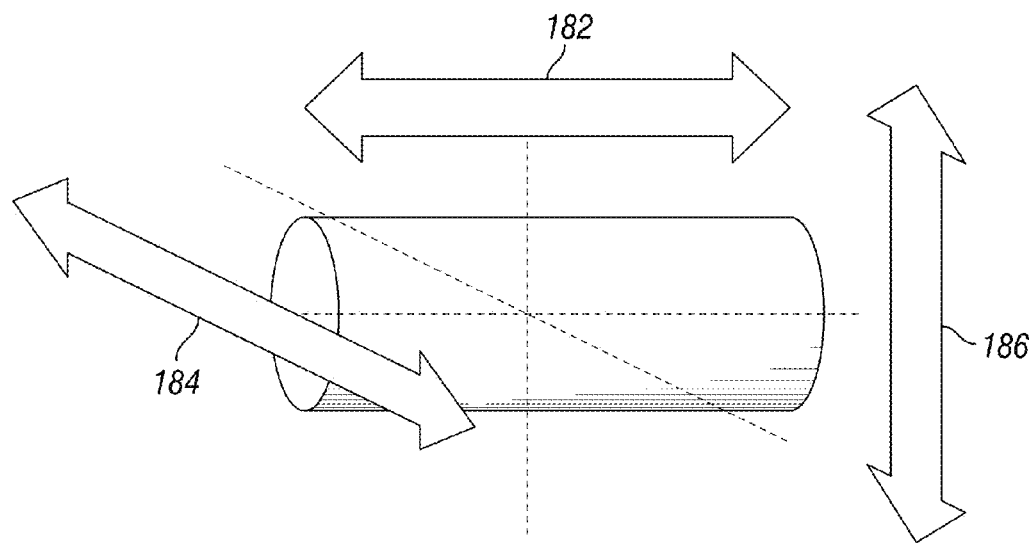

The position or orientation (FIG. 6) of the device within the vessel or tube or reservoir can be varied to minimize reverse bypass flow, maximize efficiency, maximize auto-entrainment and total flow, or alter other parameters of performance. In general, three orientation parameters (e.g. roll (176), pitch (178), and yaw (180) as shown in FIG. 6a) and three location parameters (e.g. distances along three orthogonal axes from some reference point or origin, e.g. longitudinal (182), horizontal (184), and vertical (186) as shown in FIG. 6b) can be adjusted alone or in combination. Both location and orientation can be represented in any number of other coordinate systems.

In certain embodiments and implementations, the efficiency and effectiveness of the intravascular pumping module may depend on the position and orientation of the device relative to some anatomical feature or branch vessel of the vessel or chamber the device is located in. In such cases, the proximity or location and orientation of the device relative to the anatomical feature or branch vessel of the vessel or chamber can be specified using the coordinate systems described in FIG. 6 or some other coordinate system.

In practice, the device will simply be imaged and manipulated until it is in the correct position and orientation.

In embodiments in which the device is within a vessel or chamber of approximately cylindrical shape, some of the basic orientations include axiosymmetric, axis-parallel, axis-intersecting, and skew (FIGS. 12A-1 to 12D-2). In an axiosymmetric embodiment (FIGS. 12a-1 and 12a-2), the longitudinal axis (132) of the vessel or chamber (134) and the longitudinal axis (136) of the device (138) are the same. In other words, the tube (134) and device (138) share the same axis passing through the center of each. In an axis-parallel embodiment (FIGS. 12b-1 and 12b-2), the longitudinal axis (146) of the device (144) is parallel to the longitudinal axis (142) of the vessel or chamber (140). The perpendicular distance between the two axes can be varied from zero (an axiosymmetric embodiment) to roughly the radius of the vessel or chamber (at which point the device is against the wall of the vessel or chamber). In an axis-intersecting embodiment (FIGS. 12c-1 and 12c-2), the longitudinal axis (150) of the device (152) intersects the longitudinal axis (148) of the vessel or chamber (156) at a point (154), so the longitudinal axis (150) of the device (152) and the longitudinal axis (148) of the vessel or chamber (156) lie in the same plane. As such, the axes are not parallel and intersect. While the axes intersect, the device (152) itself may or may not intersect the longitudinal axis (148) of the vessel or chamber (156). In the embodiments where the device itself does not intersect the longitudinal axis (148) of the vessel or chamber, the axes intersect at a point (154) away from device (152). In a skew embodiment (FIGS. 12d-1 and 12d-2), the longitudinal axis (162) of the device (160) and the longitudinal axis (164) of the vessel or chamber (158) do not lie in the same plane. As such, the axes are not parallel and do not intersect.

In the body, the assumption of the vessel or chamber being a straight cylinder will only be approximate. In these cases, the positions and orientations described in FIGS. 12A-1 to 12D-2 may serve as descriptions of the approximate or nominal or desired or intended position or orientation.

Given a particular orientation (including, but not limited to, those described in connection with FIGS. 12A-1 to 12D-2), defining the three-dimensional location of any part of the device (e.g. its center, inlet, or outlet) fully defines its complete position and orientation. In certain embodiments, the three dimensional location of a reference part of the device may be specified by how far the device is located from a particular collateral vessel or bifurcation or valve or narrowing or bend or other change in the biological vessel. For example, the three-dimensional location of a reference part of the device may be specified by its distance from the aortic valve or the aortic arch or the renal arteries or the iliac bifurcation or any other such biological landmarks.

Figure 13:
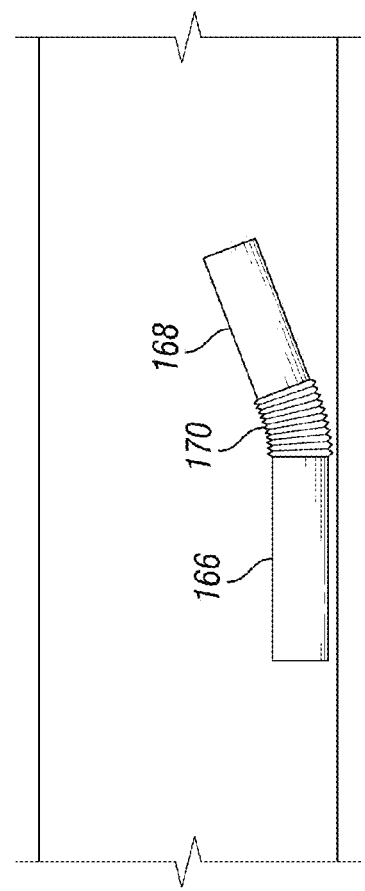
FIG. 13 is an illustrative embodiment of devices with a flexible cannula.

Adjusting Position and Orientation of Multiple Components. In embodiments in which the device comprises one or more flexible cannulas, the position or orientation of each rigid section can be independently adjusted. FIG. 13 shows an embodiment with an axis-parallel component (166) and an axis-intersecting component (168) connected by a flexible cannula (170).

Figure 32:
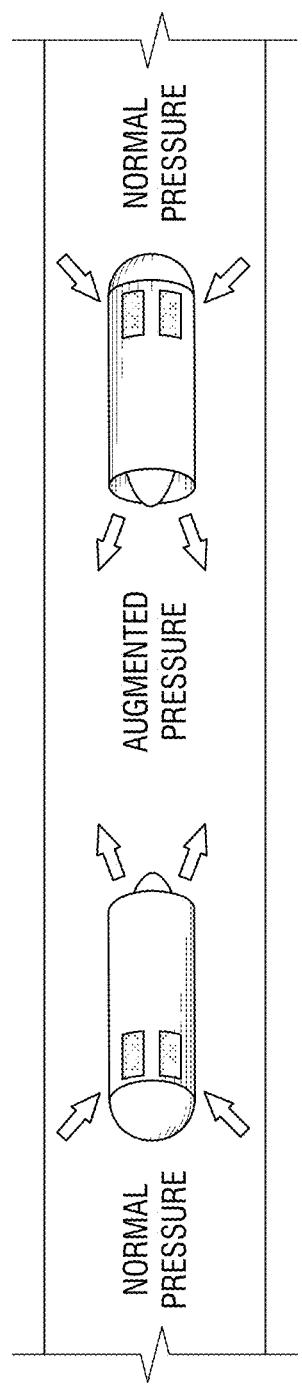
FIG. 32 shows two pumps working together to produce a limited region of high pressure.

An embodiment of the present invention for enhancing circulation or perfusion may comprise any number of pumps or cannulas or inlets or outlets. Examples of some multi-pump configurations are shown in FIG. 26. Multiple pumps may be useful for increasing or enhancing circulation or perfusion beyond what a single pump is capable of, providing the same power or motive flow in a small diameter (by using multiple smaller diameter pumps to match the power of a single, larger diameter pump), or better localizing the region of augmented pressure or flow. FIG. 32 illustrates how two pumps could be combined to create a limited area of higher pressure with minimal effects to other areas.

Additionally, two or more pumps 110, 110' may be placed in series or in parallel in the descending aorta with one pump being designed in a more cranial position and the other pump in a more caudal position, so as to allow for redundancy of the pumps in case one fails and to allow for more pumping capability while utilizing the same French size sheath for delivery, as shown in FIG. 1D. In some embodiments, the one or more pumps may be aligned so that the outlet of one pump feeds the inlet of another pump. In some embodiments, the outlet of a first pump may be positioned next to the inlet of second pump with the outlet of the first pump being offset from the inlet of the second pump. In some embodiments, the outlet of a first pump may be positioned to face the outlet of a second pump. In some embodiments, the inlet of a first pump may be positioned to face the inlet of a second pump.

In general, any number of motors, impellers, and cannulas can be connected in series or in parallel together to create a single device. FIG. 26A-26D shows three examples of embodiments with multiple motors or pumps or cannulas. FIG. 26 shows combinations of the embodiment of the device described in FIG. 10 to illustrate some basic configurations. Many other configurations and combinations are possible and useful and may not require all of the device components shown in FIG. 10 or may contain additional components. The configurations shown in FIG. 26 a, b, c, and d (and, in general, any configuration) may instead function with flow reversed from the flow direction indicated.

Figure 26A:
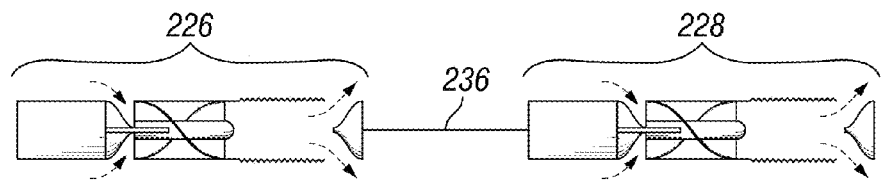
FIGS. 26a-26d are illustrative embodiments of devices utilizing multiple motors, pumps, and/or cannulas.
Figure 26B:
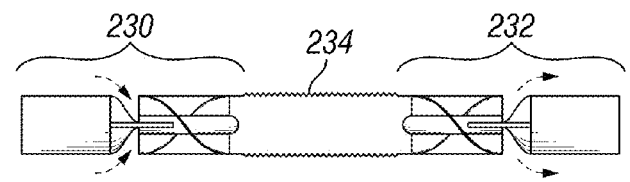
Figure 26C:
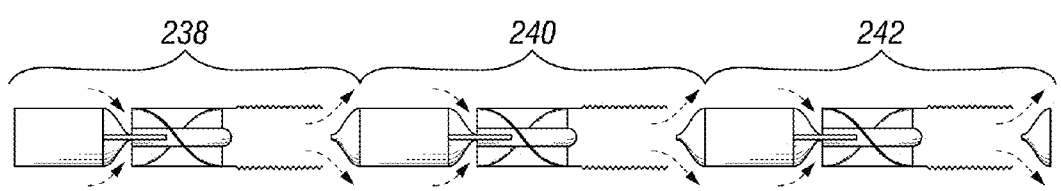
Figure 26D:
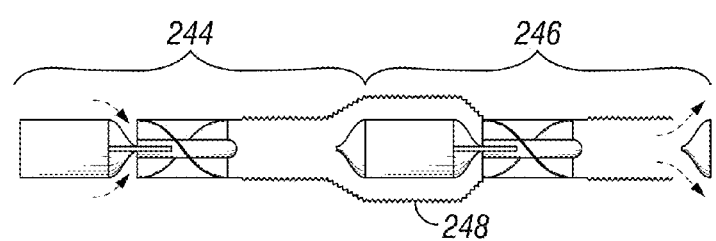
Figure 27A:
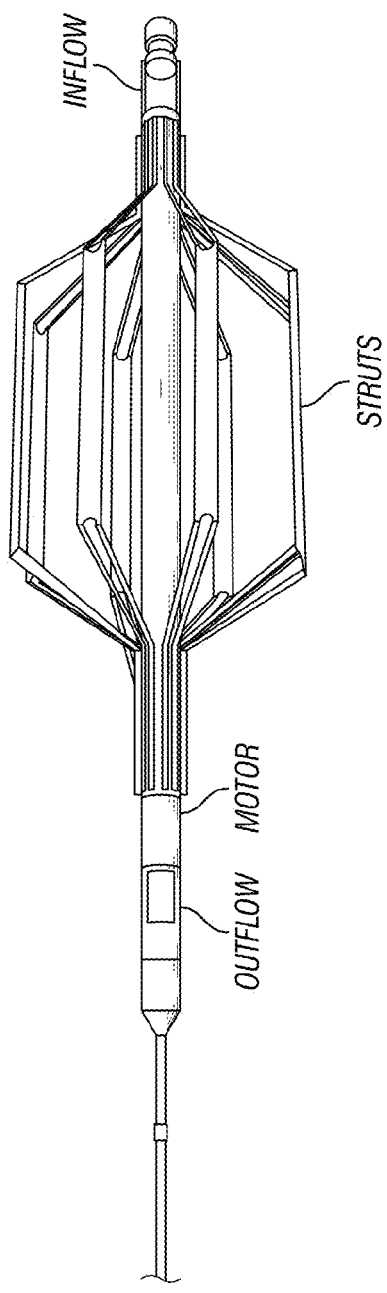
FIG. 27A is an illustrative embodiment of intravascular pumping module with struts deployed.
Figure 27B:
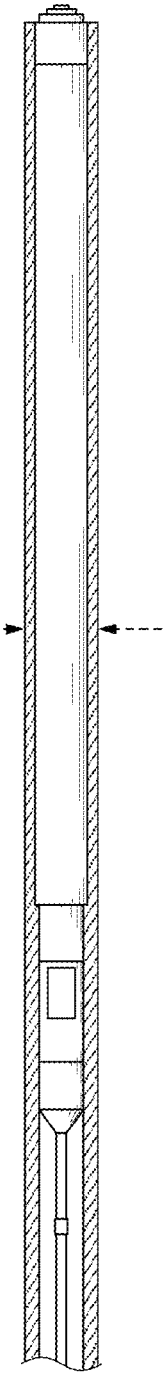
FIG. 27B is an illustrative embodiment of intravascular pumping module in a sheath.
Figure 28C:
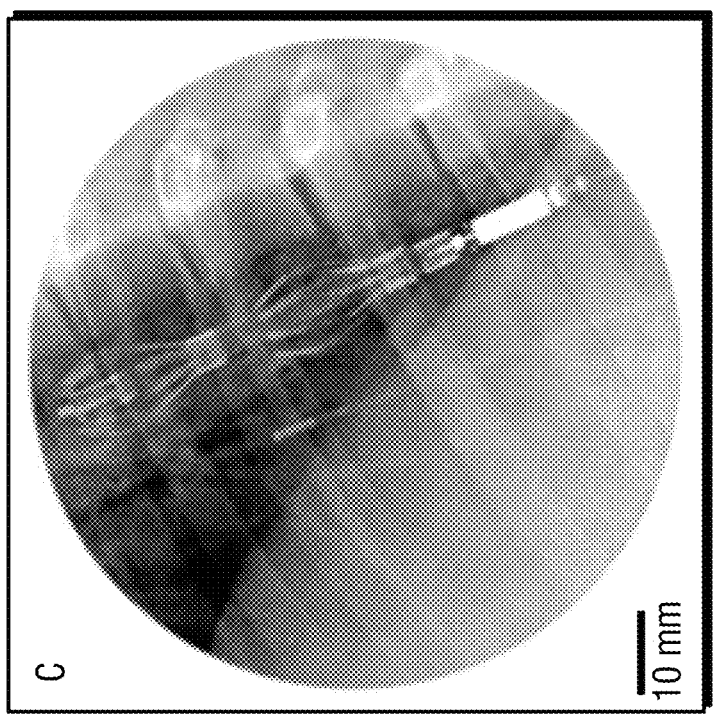
FIG. 28C shows the intravascular pumping module implanted in the descending thoracic aorta superior to splanchic arteries.
Figure 28B:
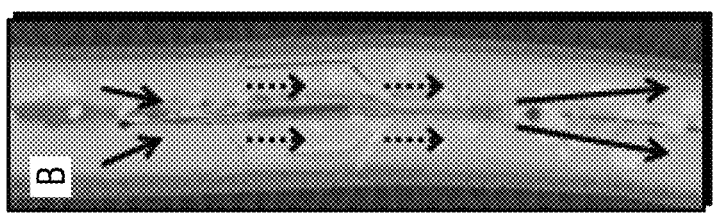
FIG. 28B is an enlarged view of intravascular pumping module implanted in a vessel.
Figure 28A:
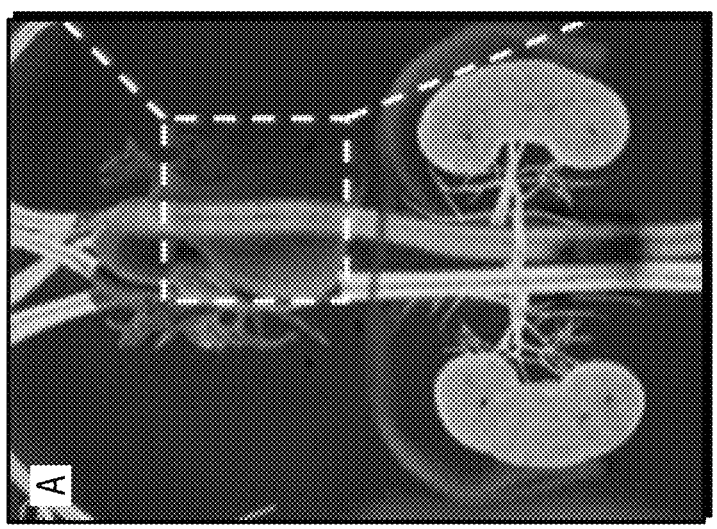
FIG. 28A is an illustrative embodiment of intravascular pumping module implanted in a vessel.
Figure 29B:
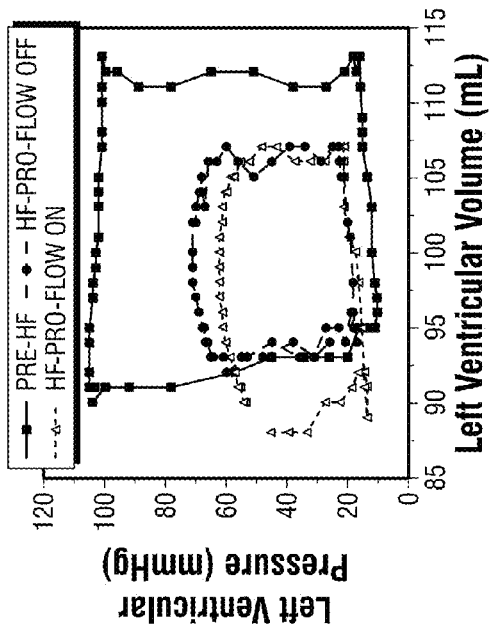
FIG. 29B shows end-systolic pressure-volume relationship (ESPVR) before heart failure and with the intravascular pumping module on or off.
Figure 29D:
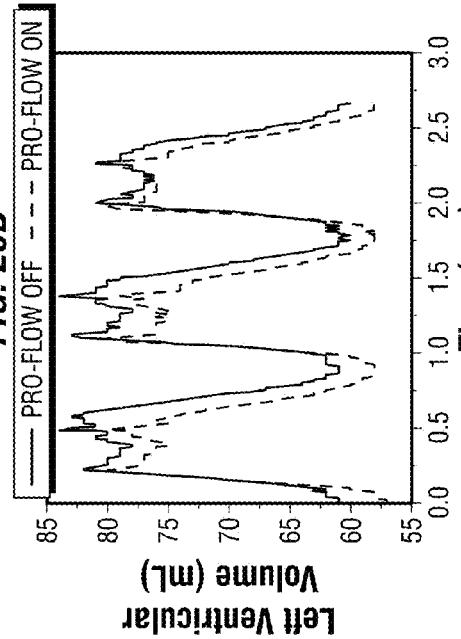
FIG. 29D shows left ventricular volume over time when intravascular pumping module is on or off.
Figure 29A:
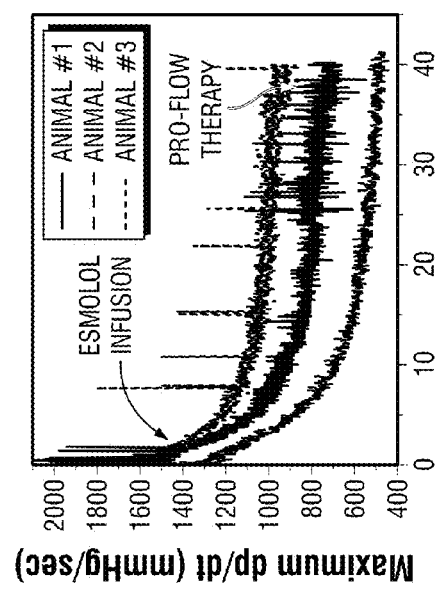
FIG. 29A shows left ventricular contractility.
Figure 29C:
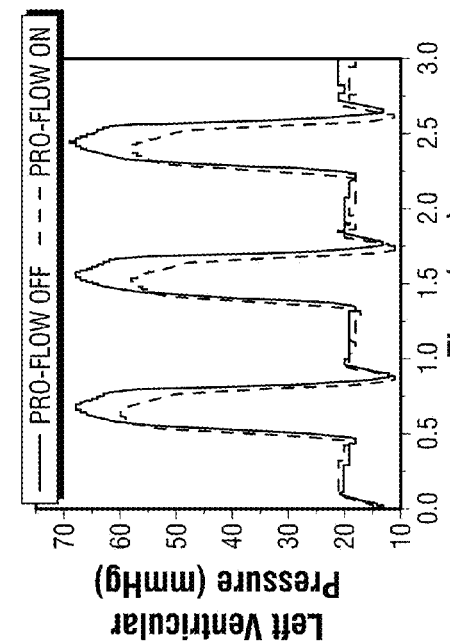
FIG. 29C shows left ventricular pressure over time when intravascular pumping module is on or off.
Figure 30:
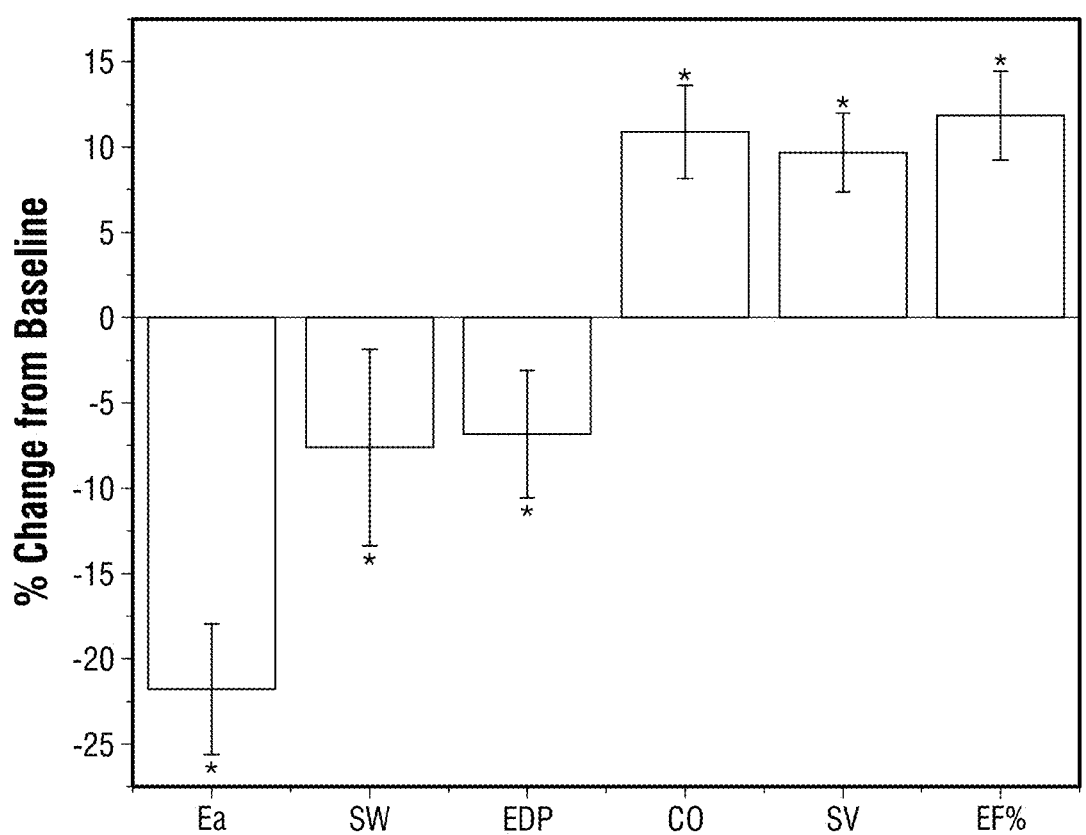
FIG. 30 shows the percentage change in Ea, SW, EDP, CO, SV, and EF %.
Figure 31:
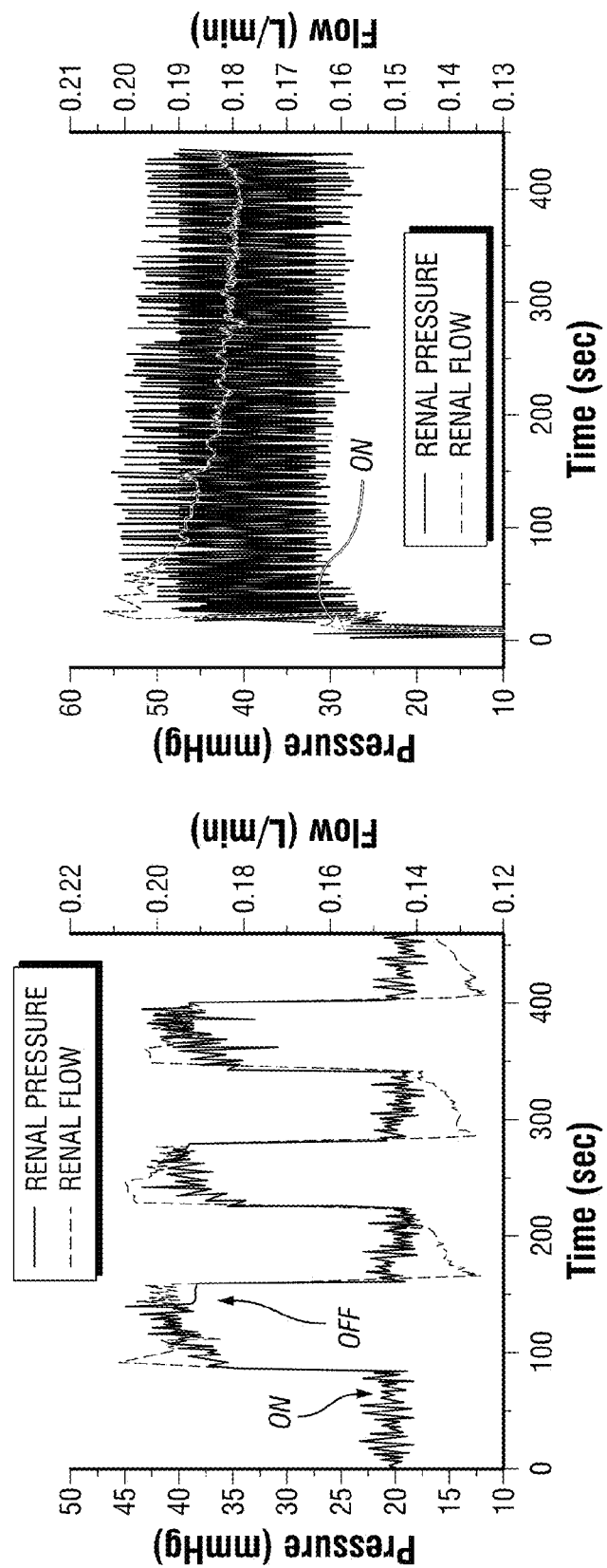
FIG. 31A shows renal flow and pressure when intravascular pumping module is on or off.
FIG. 31B shows renal flow and pressure over time.

FIG. 26a shows two instances (226 and 228) of a basic device embodiment connected by a tether (236). The tether (236) may be a power line or electrical wire or electrical cable. Outlet flow from the first device (226) mixes with the bypass flow. This configuration may be extended to any number of instances of the device. FIG. 26b shows two instances (230 and 232) of a pump portion of a basic device embodiment connected by a common flexible cannula (234). In this configuration, the ports of one pump unit (230) function as inlet ports and the ports of one pump unit (232) function as outlet ports. Further, the outlet flow from the first device (230) does not mix with the bypass flow before reaching second device (232). FIG. 26c shows three instances (238, 240, and 242) of a basic device embodiment. The outlet housing or flow director of instance (238) is connected to the motor of instance (240) and the outlet housing or flow director of instance (240) is connected to the motor of instance (242). Outlet flow from the devices (238, 240) mix with the bypass flow. This configuration may be extended to any number of instances of the device. FIG. 26d shows two instances (244 and 246) of a basic device embodiment joined as described in FIG. 26c with the addition of a flow confiner (248). The flow confiner (248) allows the outlet flow of device (244) to flow to the inlet of device (246) without mixing with the bypass flow. This configuration may be extended to any number of instances of the device. In some embodiments, the flow confiner (248) may be fashioned from collapsible material so that it increases the diameter of the device only minimally when collapsed. In other embodiments, the diameter of the flow confiner (248) may be reduced by reducing the diameter of the motor of device (246).

The dynamic performance of the circulation and perfusion enhancement system will depend on the configuration location parameters discussed above and on the motive hemodynamic power supplied by the intravascular pump module(s). The power levels required for certain performance levels may be estimated by considering a number of factors including the desired pressure and flow changes (based in part on the condition being treated), the volume and location of the region where the pressure and flow changes are desired, the native flow and resistance to flow in that region, or the number of pumps deployed. In practice, estimates of required power will typically be refined by simulation and experiment. The determination of required pump power may consider the maximum pump power required, since the applied power may be controllable and reducible to provide lower power levels when desired.

The paragraphs above have described the major parameters of the circulation and perfusion enhancement system: flow and pressure modification elements (inlets, outlets, and flow directors), system dimensions, location and orientation, number and arrangement of pumps, and pump power levels. The next step is to specify these parameters to generate flow and pressure effects that, in turn, drive circulation and pressure enhancements specifically designed to treat a particular conditions or disease state. One aspect of generating desired flow and pressure effects is designing parameter sets that produce the appropriate flow patterns in the bypass region. What this pattern should be will depend on the particular embodiment and indication, but three common targeted flow patterns are allowing recirculation, maximizing auto-entrainment, and creating a "fluid dynamic valve". Recirculation (reverse bypass flow) when the outlet effects are high pressure, low net flow, and low swirl. These conditions can be achieved with an annular output nozzle that develops radial flow. In contrast, in other embodiments, it is desirable to achieve maximal total flow or efficiency. In these cases generating stable auto-entrainment is desirable. The optimal parameter set to generate auto-entrainment will depend on the particular embodiment and hemodynamics, but a common combination is a high velocity laminar flow maximally down the lumen of the artery together with a restricted or staggered inlet. The inlet design encourages flow into the bypass region and the high velocity outlet jets generate low pressure areas that draw flow from out of the bypass region. Additionally, the central laminar flow can continue to entrain flow at some distance from the outlet through laminar velocity shear. Alternatively, nonlaminar flow directed at a slight angle to the axis of the vessel can entrain flow from the bypass region through turbulent diffusion of momentum. In yet other embodiments, auto-entrainment may be undesirable or unattainable and an appropriate flow pattern for the bypass region is a fluid dynamic valve. This is a flow pattern that prevents recirculation but has essentially zero net flow. A standing swirl (circumferential velocity) is a common example.

This simple and nonlimiting perspective on possible flow patterns in the bypass region is enough to develop parameter sets for treating particular conditions or disease states by targeting specific (i.e. magnitude and location) circulation and perfusion enhancements.

Conditions in which targeted, localized, short-term or long-term circulation improvement may be desirable or beneficial may include, but are not limited to: heart failure (assist in moving blood away from the heart), compartment syndrome (reduce flow to allow pressure drop in affected area), kidney issues and complaints including AKI, sepsis, shock (including cariogenic shock, hypovolemic shock, and hemorrhagic shock), Raynaud's phenomenon, poor peripheral circulation (peripheral vascular disease), chronic venous insufficiency (edema), poor perfusion of the small or large intestines or conditions possibly resulting from such poor perfusion, hypervolemia (possibly to increase kidney function), hypovolemia (to maintain perfusion of key organs), tachycardia/bradycardia (through regulation of afterload and aortic pressure), poor circulation due to obesity, peripheral neuropathies caused diabetes mellitus or other causes, cystic fibrosis, or fluid in the lungs Embodiments of the present invention may be used to increase or enhance circulation or renal (or other end-organ) perfusion for short-term or long-term durations. Embodiments of the present invention used to enhance circulation or perfusion may or may not use or include or represent all aspects or characteristics of the present invention. For example, in some cases, the diameter of the device may be roughly equivalent to the blood vessel the device is located in. In such cases, bypass flow and auto-entrainment may be less important whereas other characteristics or aspects of the current invention, such as axial inlet and outlet port design, will be more important to achieving sufficient enhancement to circulation or perfusion.

For many embodiments of the circulation and perfusion enhancement system targeting treatment of many different disease states, developing a suitable parameter set (including, for example, but not limited to, determining the nozzle designs and power levels that provide the greatest net flow under various native flow and pressure profiles) will be an iterative process involving computational fluid dynamics, in-vitro simulations, animal experiments, and controlled human clinical trials. The availability of data from these simulations and experiments, along with evolving ideas from clinicians and researchers about what the most desirable circulation and perfusion enhancements for treating various conditions or disease states, will build better information about the use of the present invention to provide those treatments. The currently presented parameter sets, flow and pressure effects, and circulation and perfusion enhancements listed for each condition below are nonlimiting examples of basic approaches.

Summary Example Embodiments for Various Diseases Conditions. The conditions provide a mix of chronic and acute conditions that would have a range of treatment durations from several hours to several months. The paragraphs below describe example embodiments of the intravascular pumping module using one pump. These example embodiments discuss specific implantation locations, but it will be clear to those of ordinary skill in the art that a range of locations will be suitable in each case, that if the described locations are for some reason unsuitable, other locations can be used, and that the flow and pressure modification elements of the present invention can be used from a broad range of potential implantation locations to gain greater or more specific improvements in circulation or perfusion in the region of interest than a blood pump designed for non-specific systemic circulation enhancement would provide. Additionally, effectiveness of these treatments does not depend on matching all system parameters. For example, substantially increased net flow can be can be generated without auto-entrainment and without swirl reduction. Substantial improvement over non-specific systemic circulation enhancement is achievable through coarse adjustment of just the basic parameters of outlet flow direction and velocity. Finer adjustment of those or other parameters can increase the effectiveness and efficiency of the intravascular pumping module.

Note that those of ordinary skill in the art may have differing opinions of what specific circulation and perfusion enhancements would provide the most effective treatment for a particular condition. These opinions may change over time as new studies and research provide new data. The examples below are not meant to be limiting in any way, but rather to demonstrate the flexibility of the intravascular pumping module in providing whatever specific circulation and perfusion enhancements are desired.

The first example embodiment, for treating heart failure, will be explored in detail to illustrate how the flexibility and configurability of the circulation and perfusion enhancement system can generate the specific circulation and perfusion enhancements identified.

Heart Failure: One dimension of heart failure is unloading of the left ventricle to rest the heart. This treatment approach can be thought of as essentially reducing the systemic vascular resistance that the heart pumps against. Such unloading also treats the related conditions of pulmonary venous hypertension and cardiogenic pulmonary edema.

In one approach to resting the heart as much as possible, the desired effects of the circulation and perfusion enhancement system are maximal net flow increase in the aorta (to assist the heart in moving blood around the body) and reduced aortic root pressure (to reduce the pressure the heart ejects blood against during systole). Note that VADs (whether traditional, less-invasive, or percutaneous) assist in circulation but typically increase pressure in the aortic root. Other treatments, like inter-atrial shunts, reduce pre-load but not aortic pressure.

To assist general systemic circulation, the circulation and perfusion enhancement should be placed in the aorta before major branch vessels divide the flow. This consideration suggests placement above the celiac artery. The pressure drop upstream of the device increases as the volume of blood upstream of the device decreases. For this reason, placing the device closer to the aortic root generates greater pressure drops in the aortic root.

In a particular embodiment, consideration of a number of factors might lead to a placement in the descending thoracic aorta behind the heart and above the diaphragm: first, placement downstream of the carotid artery branches virtually eliminates risk of a stroke caused by the device; second, sufficient blood volume upstream of the device should be maintained so as to not drop aortic root pressure too low; third, the outlet flow of the device can be better directed once the aorta straightens after the aortic arch.

To encourage high net flow, the outlet of the circulation and perfusion enhancement device should have high auto-entrainment and low recirculation in the bypass region and direct its outlet flow along the direction of native flow with low swirl. These factors are consistent with configuring the device outlet to produce a laminar or low turbulence jet directed along the axis of the aorta. This imparts momentum in the direction of native flow without the circumferential flow component of swirl, reduces the possibility of recirculation by moving pumped blood away as fast as possible, and encourages auto-entrainment through shear between the outlet jet and the surrounding native flow.

In summary, to generate the desired effects in this potential embodiment, the circulation and perfusion enhancement system is oriented for downward flow in the thoracic aorta with the outlet at above the diaphragm at T6-T8. The flow control elements are configured to produce maximally downstream (i.e. in direction of native flow) flow with low turbulence, auto-entrainment, and minimal downstream swirl. The duration of this treatment may last from one to six months. A similar circulation and perfusion enhancement, but for hours instead of months, may be beneficial in providing cardiac support and unloading to post myocardial infarction or post cardiac surgery patients. One potential benefit of the circulation and perfusion enhancement discussed is the reduction in aortic root pressure with preserved flow. This reduced pressure could help prevent or reduce reperfusion injuries to the heart during its recovery period.

The above examples give an indication of how the circulation and perfusion enhancement system can be configured to produce very specific effects. None of that discussion (or the discussion below) should be taken as limiting the potential of the circulation and perfusion enhancement system from being used to generate any possible circulation or perfusion enhancement for any disease or condition from any possible implantation site.

In the following example embodiments, the discussion for each disease or condition begins with an assumption of the specific effects desired from the intravascular pumping module.

Kidney Dysfunction: The assumed desired effect in this example embodiment is increased pressure at renal branching. To generate this effect, the circulation and perfusion enhancement system is oriented for downward flow in the abdominal aorta with outlet just above both renal branches (T12-LI). The flow control elements are configured to produce high radial flow and no auto-entrainment. Note that "leakage" of the high pressure region may result in increases in peripheral circulation (downward leakage) or aortic root pressure (upward leakage); this can be mitigated, if desired or necessary, with a two pump solution. The duration of this treatment may last anywhere from several hours to several months depending on the underlying condition. A similar circulation and perfusion enhancement, but may be beneficial in providing kidney support during surgical procedures using cardiopulmonary bypass. A significant fraction of such procedures lead to serious kidney injuries and need for dialysis. It is possible that enhanced kidney perfusion during and following the procedure could reduce this risk (potentially by lowering pressures at certain points to prevent reperfusion injuries).

Cardio-Renal Syndrome: The assumed desired effects in this example embodiment are reduced aortic root pressure and net flow increase together with increased pressure at renal branching (compromise between heart failure and kidney dysfunction treatments). To generate these effects, the circulation and perfusion enhancement system is oriented for downward flow in aorta between arch and renal branching (outlet at T9-T10). The flow control elements are configured to produce 45 degree flow with fluid dynamic valve to minimize recirculation, reduced downstream swirl. Note that the extension of high pressure region past branching area may result in increases in peripheral circulation; this can be mitigated, if desired or necessary, with a two pump solution.

Endothelial Dysfunction: The assumed desired effects in this example embodiment are net flow increase with high swirl. To generate these effects, the circulation and perfusion enhancement system is oriented for downward flow in thoracic aorta at/above diaphragm (outlet at T6-T8). The flow control elements are configured to produce maximal swirl downstream of outlet with no reduction in net flow.

Sepsis: The assumed desired effects in this example embodiment are increased end organ perfusion with reduced peripheral circulation. To generate these effects, the circulation and perfusion enhancement system is oriented for upward flow just above aortic bifurcation. The flow control elements are configured to produce maximally upstream flow (i.e opposite direction of native flow) with minimal swirl. Note that the extension of high pressure region upstream may result in increases in aortic root pressure; this can be mitigated, if desired or necessary, with a two pump solution.

Aneurysm: The assumed desired effects in this example embodiment are focused pressure reduction in region of aneurysm or other aortic defect, with the system positioned away from the aneurysm or defect. To generate these effects, the circulation and perfusion enhancement system is fitted with an outflow cannula, oriented to discharge in the direction of native flow, and positioned upstream of the aneurysm or defect with the outflow cannula extending through to the downstream side of the aneurysm or defect. The flow control elements are configured for moderate flows and minimal downstream swirl.

The above nonlimiting examples illustrate the novel benefits of the circulation and perfusion enhancement system. Further examples will be described more briefly.

Peripheral Vascular Disease may respond to embodiments that place the pumping modules in the iliac arteries or at the base of the aorta, configured to raise pressure and flow in the leg arteries.

The circulation and perfusion enhancement system could be placed and configured for wound healing or post surgical support by targeting major supply arteries to the surgical site. A nonlimiting examples of this include creating perfusion changes in the iliac artery for a leg injury or in the celiac artery for liver surgery. The treatment may involve decreased perfusion initially to prevent inflammation and reperfusion injuries and increased perfusion later to promote healing and cell growth. Similar approaches could increase perfusion to the same areas to treat non-specific or idiopathic injuries.

The circulation and perfusion enhancement system could provide perfusion changes directed toward particular end-organs (or even parts of particular end-organs through placement in the celiac, SMA, IMA, or gonadal arteries) and coordinated with chemotherapy or other cancer treatments to improve efficacy or reduce side effects. For blood borne chemotherapeutics, perfusion of susceptible organs could be reduced. Alternatively, perfusion of the tumor could be reduced to enhance other treatments.

The circulation and perfusion enhancement system could be configured to produce small and controlled reductions in flow and pressure in the celiac artery that may promote weight loss. This active and controllable approach may be superior to a static obstruction which, if too restrictive, could lead to tissue death.

The circulation and perfusion enhancement system can provide key regions of the body with relief from chronic hypertension. As a nonlimiting example, the example embodiment discussed above in connection with heart failure reduces blood pressure in the carotids, coronaries, and aortic root—all key risk areas susceptible to high blood pressure. Reducing pressure in these areas (even by increasing it in other regions) could potentially decrease the severity of the underlying hypertension.

The circulation and perfusion enhancement system could be located in the pulmonary artery to increase blood flow through the lungs and reduce effective pulmonary vascular resistance. This embodiment may provide an effective treatment for pulmonary arterial hypertension and help prevent right heart failure. This placement would require the power wire to cross the tricuspid and pulmonary valves.

Note that many diseases or conditions occur in combination and are thought to be inter-related. One example is heart failure and kidney dysfunction, the combination of which is sometimes referred to as cariorenal syndrome. It will be apparent to one of ordinary skill in the art that system parameters can be adjusted to provide a mix of the desired effects for treating each condition.

Many variations of these example embodiments are possible including, but not limited to, changing the orientation of the pumping module in radial flow cases, using additional pumps, changing power levels, or making small changes in various other parameters.

Method of Providing Disease or Condition Appropriate Therapy

The major steps in using embodiments of the present invention to enhance circulation or perfusion by altering or augmenting or enhancing pressure and flow are: Step 1) Select the appropriate class of device for the condition being treated and the targeted or desired pressure and flow augmentation. Step 2) Select the appropriate size and make final adjustments based on patient specific factors. Step 3) Locate and Orient the Device. Step 4) Operate the Device. Step 5) Remove the device. These steps are discussed more fully below.

Step 1: Select the appropriate class of device for the condition being treated and the targeted or desired pressure and flow augmentation Step 2: Select the appropriate size and make final adjustments based on patient specific factors Step 3a: Implantation alternative 1. The method or procedure to transluminally implant the intravascular pumping module 80 of the present invention may include some, or all, of the following steps. First, the patient is prepared in a catheterization lab in a standard fashion. Under conscious sedation, local anesthesia is applied to the femoral area, similar to the manner in which a standard heart catheterization is performed. A small 3 cm incision is made in the vertical plane overlying the femoral artery 10, just below the inguinal ligament. The femoral artery is exposed, and may then be entered by the Seldinger technique over a guide-wire and is successively dilated to allow entry of a sheath 140, having a preferred diameter of 21 French (FIG. 1B). The sheath 140 is then passed over a guide-wire and then placed into position in the descending aorta 98 or other vessel or chamber, with the tip 141 (FIG. 1B) in the mid thoracic aorta, superior to splanchnic arteries. The sheath 140 is then de-aired. Sheath 140 contains at its external end, outside the patient's body, a one-way valve and a side arm for de-airing. The intravascular pumping module 80 is then passed through the one-way valve into the sheath 140 to the tip 141 at the mid thoracic area. The passage of the intravascular pumping module 80 through the sheath 140 is made possible with an obturator (not shown). As the obturator is held in place, the sheath 130 is then withdrawn, which in the case of a spring type support structure 120, the support members, or struts 121 then spring open and anchor the pump 110 in the descending aorta 98 or other vessel or chamber, or alternatively, if support structure 120 is a self-expanding stent 200, stent 200 springs open and anchors the pump 110 in the aorta 98 or other vessel or chamber. The obturator is then removed, and the sheath 140 is then pulled back with the power wire 117 still passing through, or disposed within, the sheath 140. Power can then be applied to the power wire, either directly or through the controller, to begin operation. Subclavian approach: Alternatively, rather than transluminally implanting the intravascular pumping module 80 of the present invention through the femoral artery, as previously described, intravascular pumping module 80 may be transluminally implanted and delivered through the left or right subclavian artery, and the power source or battery and controller may be placed in the pectoral area of the patient. This type of implant technique would be similar to the implantation of a cardiac pacemaker or defibrillator, with the exception that access would be obtained through the subclavian artery, rather than the subclavian vein. The power source, and/or its controller, may be incorporated in a device such as a cardiac pacemaker or defibrillator, if used in this manner. The implantation method discussed above is provided for illustrative purpose only. It will be recognized by one of ordinary skill in the art that the intravascular pumping module 80 may be implanted in other locations utilizing any suitable implantation method known.

Step 3: Implantation alternative 2. Prior to the implantation procedure, examine the patient and use externally observable anatomical landmarks to estimate the desired position of the device. Place one or more adhesive radiopaque markers on the body so that the desired position of the device can be observed by fluoroscopy. For example, place markers on both sides of the body so that a line drawn between them passes through the estimated required position of the device. In this example, the desired position of the device will appear in between the two markers. Place the patient in the cath-lab and follow standard procedures to prep the patient for a catheter procedure. Using standard cath-lab techniques and standard access sites for the target vessel or chamber, advance a guidewire through the appropriate vessels or chambers to or past the estimated implantation site as marked by the externally affixed radiopaque markers. Using imaging (e.g. dye and fluoroscopy, intravascular ultrasound) measure the diameter of the vessel or chamber at the implantation site to verify allowable device dimensions. Prepare a device with the appropriate hemodynamic features and dimensions. The device is placed in its pre-deployment configuration inside one end of a sheath long enough for the other end to remain outside the body when the device is advanced to its implantation site. The sheath contains an obterator that reaches the end of the device and extends out of the sheath on the other side. The devices power wire and a snare wire extend from the end of the device, through and past the end of the obterator. The power wire is connected to the device. The snare wire is enclosed on the retrieval hook or slot at the end of the device. Assembly of these delivery packages for a number of devices with a range of dimensions may take place well in advance of the procedure. Using standard cath-lab techniques, including dilators and introducers, to provide large bore access at the access site. Using standard cath-lab techniques, introduce the entire delivery package (device, sheath, obturator, power wire, and snare wire) into the vessel at the access site with no relative motion between the components of the delivery package. Advance the entire delivery package, with no relative motion of the components, until the device sits at its intended implantation site as determined by the alignment of the device and the external radiopaque markers as observed by fluoroscopy. While holding the obturator in place to maintain device position, pull the sheath slowly out of the vessel until the struts and any other collapsed features are exposed and in their expanded deployment position. Verify the deployed position of the device and its struts by fluoroscopy. If the deployment is not satisfactory, hold the device in place by tension on the snare wire and advance the sheath to collapse the struts back to their pre-deployment configuration. Once this is complete, the device can be repositioned and redeployed by once again pulling the sheath back away from the device. Once the deployed position of the device and its struts is verified, release the snare wire from the retrieval hook or feature and withdraw it through the obterator. Withdraw the obterator and sheath completely. Close the vessel access with standard cath-lab techniques for large bore devices. If desired, for longer treatment durations (over seven days), an implantable electronics package may be used. In this case, tunnel the power wire under the skin to the approximate desired site of the implantable electronics package. Options: Guidewire is optional. Entire procedure could take place without fluoro, at least for simpler implantations like in the aorta. The radiopaque markers are optional. Observable anatomic markers (like the diaphragm) or ad hoc markers (like surgical tools set on the patient's body) could be used instead. Snare wire is optional. The power wire could be made strong enough to be used instead or the device could be implanted with no immediate option for re-sheathing. In this last case, the retrieval process could be followed if retrieval or repositioning is needed.

Figure 34A:
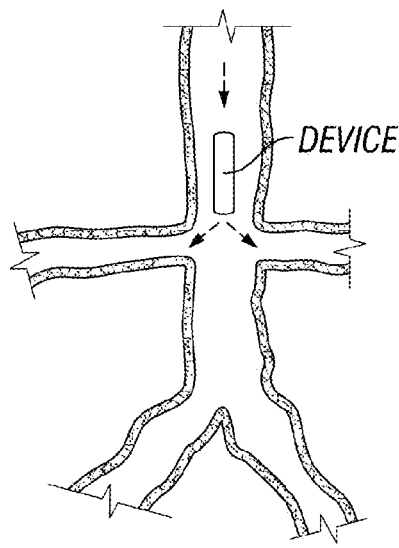
FIG. 34A shows a device placed upstream of the renal arteries.
Figure 34B:
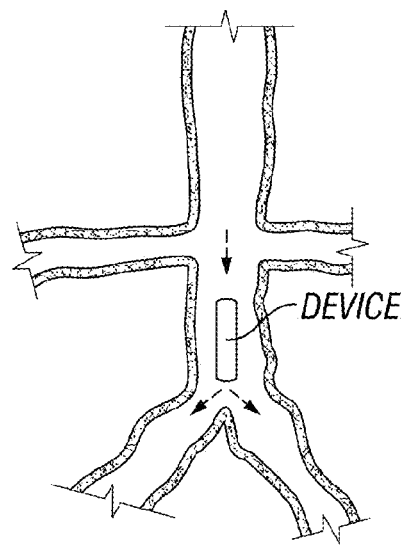
FIG. 34B shows a device placed at the iliac bifurcation.
Figure 34C:
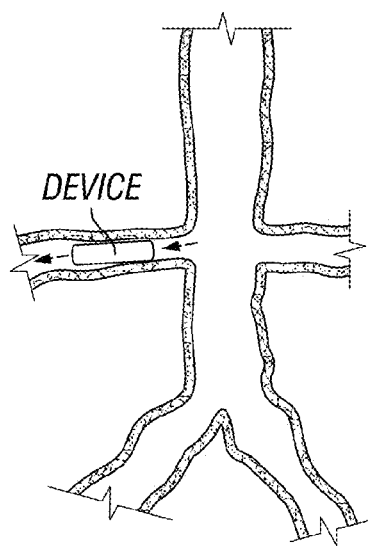
FIG. 34C shows a device placed in a renal artery.
Figure 34D:
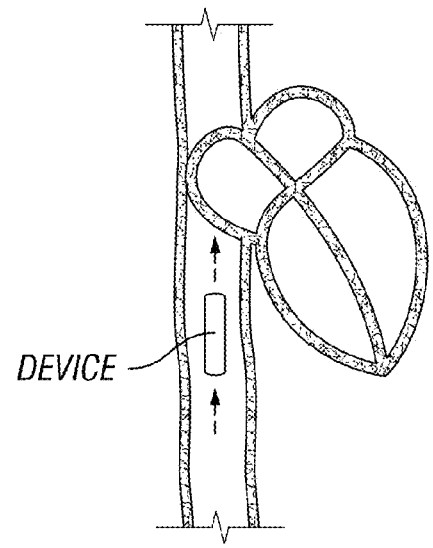
FIG. 34D shows a device placed in an inferior vena cava.
Figure 35:
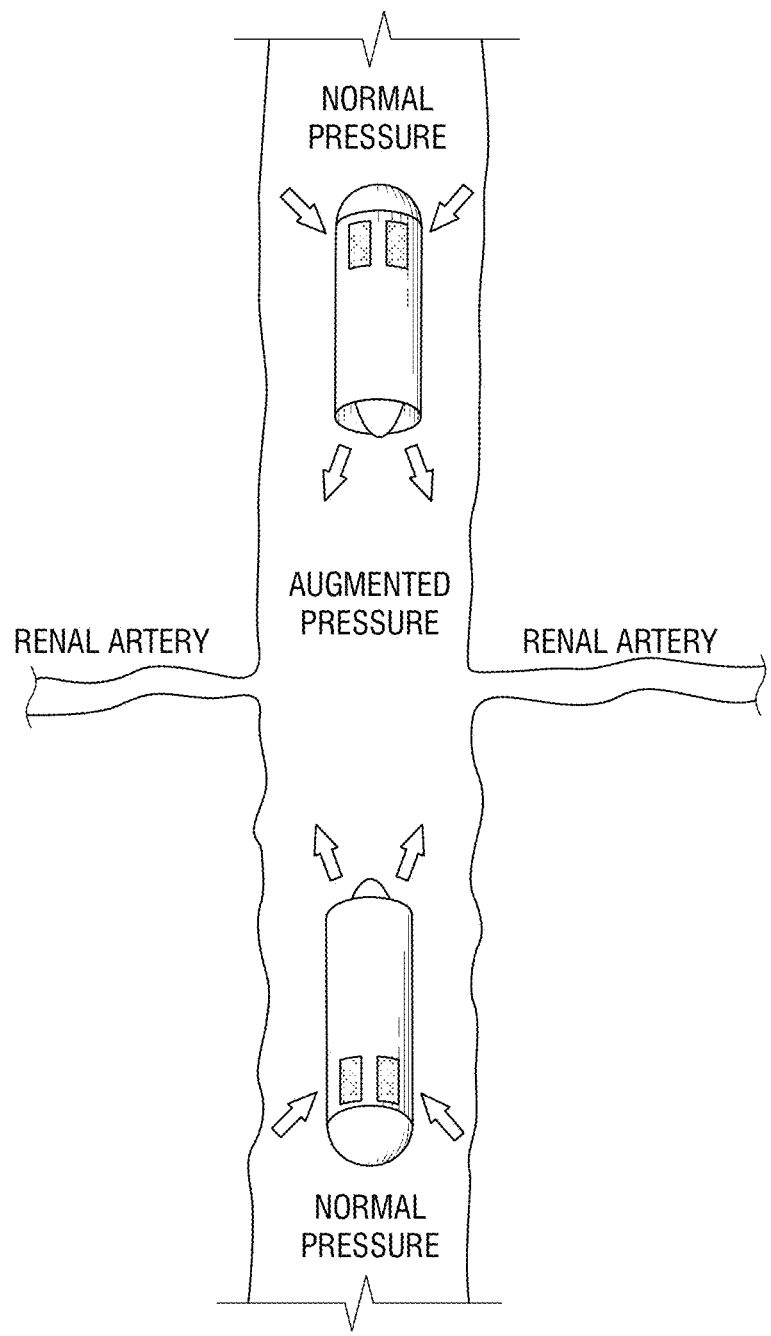
FIG. 35 shows a two-pump embodiment for renal perfusion.

Step 3b: Implantation alternative 2. Locate and orient the device for the condition being treated and the targeted or desired pressure and flow augmentation. To achieve series flow and/or pressure augmentation through auto-entrainment, the device is placed within the vessel or chamber in the proper location and orientation. Localizing or limiting or targeting or focusing the augmented blood flow and blood pressure to one organ or region or area of the body may be useful to achieve desired enhancements in circulation and perfusion in one area of the body without unnecessarily impacting other areas of the body. One set of major factors in such localizing or limiting or targeting or focusing includes adjusting pump location or position or orientation within the vasculature or blood vessel. The changes to flow or pressure in a blood vessel or vessels created by the device (and therefore the enhancement to circulation or perfusion) may be adjusted or modified or impacted by altering the location of the device within the vasculature or circulatory system or by altering the position and orientation of the device within a particular blood vessel. In general, and as discussed in connection with FIG. 6, any of three orientation parameters (e.g. roll, pitch, and yaw) or any of three location parameters (e.g. distances along three orthogonal axes from some reference point or origin) may be adjusted alone or in combination. Examples of some of the basic orientations that may be used for enhancing circulation or perfusion by altering or augmenting or changing flow and pressure are discussed in connection with FIG. 12. Given a particular pump orientation (including, but not limited to, those described in connection with FIG. 12), specifying the three-dimensional location of any part of the device (e.g. its center, inlet, or outlet) fully defines its complete position and orientation. In embodiments meant to enhance circulation or perfusion of some region of the body, the three-dimensional location of a reference part of the device may be specified by how far that part of the device is located from a particular collateral vessel or bifurcation or valve or narrowing or bend or other change or feature or landmark of the circulatory system. For example, the three-dimensional location of a reference part of the device may be specified by its distance from the aortic valve or the aortic arch or the renal arteries or the iliac bifurcation or any other such biological landmarks. The landmarks used and the desired distances from those landmarks may depend on the design of the device, the condition being treated with enhanced circulation or perfusion, and the desired changes to flow or pressure at a given point relative to the device. The device may be held in its preferred position and orientation by mechanical struts or inflatable balloons or other support mechanisms. These struts or balloons or other support mechanisms may be located in any number of positions along the device. The struts or balloons or other support mechanisms may also serve to direct, restrict, block, occlude, or otherwise modify the flow and pressure (and the enhancements to circulation or perfusion) created by the device. FIG. 34 shows examples of an embodiment of the device located in the body to provide enhanced circulation or perfusion to specific areas of the body. FIG. 34a shows the device placed upstream of the renal arteries with an outlet flow director and nozzle designed to change pressure and flow in the renal arteries. FIG. 34b shows the device placed at the bifurcation of the aorta into the common iliac arteries to enhance circulation to the legs without increasing flow or pressure to the end-organs. FIG. 34c shows a smaller embodiment of the pump located in one renal artery to selectively enhance circulation or perfusion to one kidney only without significantly affecting circulation or perfusion in other areas of the body. In this case, the pump may take up the entire diameter of the vessel, eliminating bypass flow, but still functions effectively. FIG. 34d shows an embodiment of the device located in the inferior vena cava to enhance circulation by increasing venous return. In general, an embodiment of the present invention may be located anywhere in the vasculature its size allows. In embodiments in which the device comprises one or more flexible cannulas, the position and orientation of each rigid section can be independently adjusted as described in connection with FIG. 13. For example, FIG. 35 shows a two pump embodiment where one pump sits in the aorta above the renal arteries and the other sits in the aorta below the renal arteries. If the pumps in this embodiment both pump toward the renal arteries, the pressure and flow between the pumps (that is, affecting the renal arteries) may be strongly increased whereas the pressures and flows in regions not between the pumps may be far less strongly increased. Such focused augmentation may be useful in cases of sepsis or related conditions to increase pressure or flow in the renal arteries without stressing or increasing flow through peripheral vessels that may have been made leaky by the septic condition.

Step 3d: Position verification made by standard cath-lab techniques as familiar to those of ordinary skill in the art.

Step 4: Operate the device for the desired duration and in a manner intended to provide the targeted or desired pressure or flow augmentation with for the condition being treated. The pump is switched on. The pump portion of some embodiments of the current invention may comprise an electrical motor, the speed of which can be varied from 0% to 100% of full speed and the rotation direction of which can be reversed. In a subset of these embodiments, the speed of the motor can be varied over this range (e.g. from off to full speed or from full speed in one direction to full speed in the other direction) more than 150 times per minute. This controllability and variability of the motor speed may be used to further adjust, modify, control, or augment the pressure and flow changes the device creates. In certain embodiments, the speed or direction of rotation of the electric motor may be synchronized with the native pulse or native pressure or native flow in the vessel the device is located in. Such synchronization may allow differential augmentation of systolic or diastolic pressure and flow. In other embodiments, the speed or direction of the motor may be preset to change and vary over time without regard to native pulse or native flow or native pressure. This preset change in speed or direction may occur on an arbitrary timescale. Alternatively, the changes in speed or direction of the electric motor of the pump device may be synchronized to some signal from a sensor of body status or function, to some signal from an internal or external control unit, or to input from the patient or his doctor. The pumping system of the present invention may be intended for short-term use to increase circulation or perfusion in some organ or region of the body on an acute basis. The pumping system of the present invention may be intended for long-term use to increase circulation or perfusion in some organ or region of the body on a chronic basis.

Step 5: Remove the device. Many embodiments of the present invention may be removed or relocated by catheter if treatment is complete or if the device is not working properly or to move or relocate or adjust or modify the circulation or perfusion enhancement created by the device. The pump 110 and support structure 120, including support members 121, could be designed whereby pump 110 and support structure 120 could be removed with a catheter based removal device (not shown) which could collapse support members 121 and disengage them from their anchored configuration to permit the removal of them and pump 110, if desired, such as to replace or repair pump 110. Such a catheter based removal device could be similar to those presently used with inferior vena cava filters.

Figure 38:
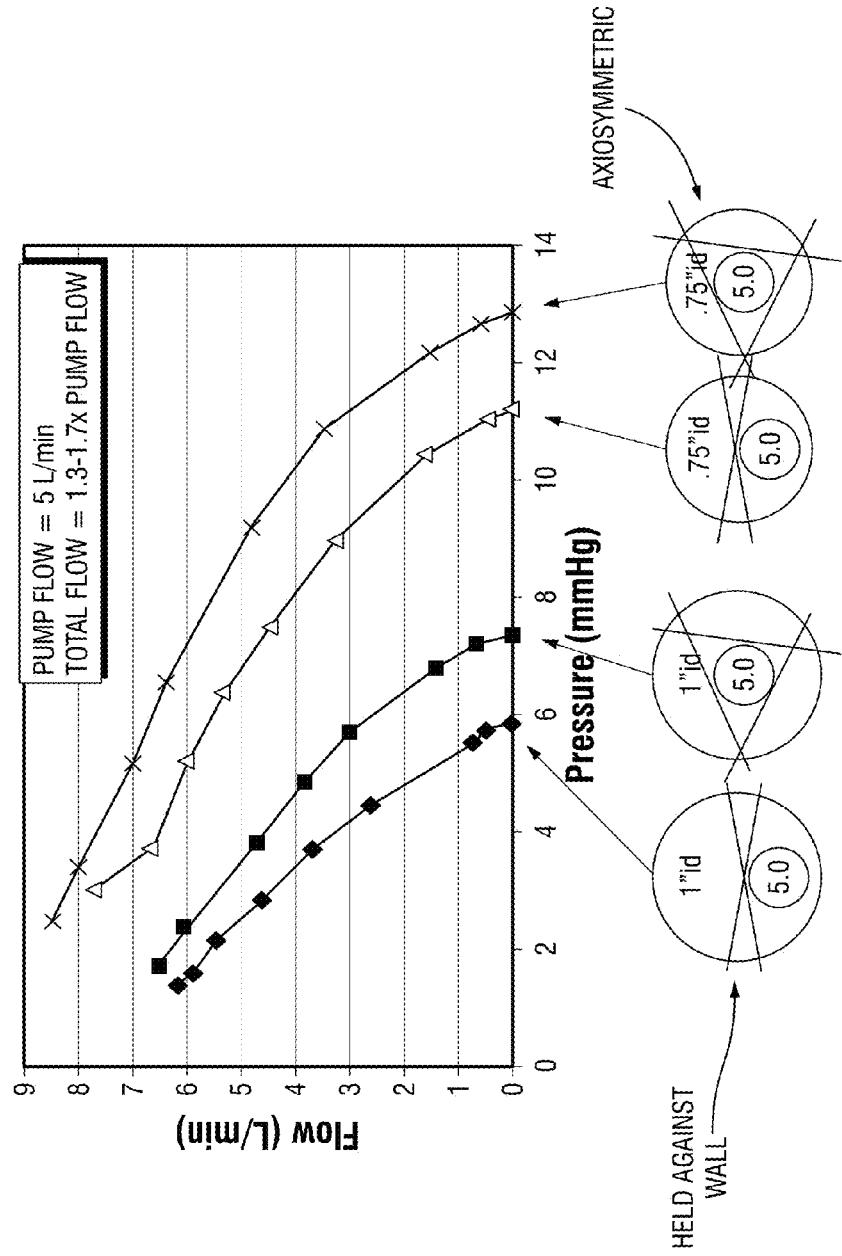
FIG. 38 shows results of bench top experiments on auto-entrainment.

Experimental Example (FIG. 38). The following examples are included to demonstrate particular aspects of the present disclosure. It should be appreciated by those of ordinary skill in the art that the methods described in the examples that follow merely represent illustrative embodiments of the disclosure. Those of ordinary skill in the art should, in light of the present disclosure, appreciate that many changes can be made in the specific embodiments described and still obtain a like or similar result without departing from the spirit and scope of the present disclosure.

Experimental and Supporting Data. Early in vitro studies showed that our device in a low resistance flow loop was capable of generating a 13 mmHg pressure gradient and producing up to 8.5 L/min of flow. Ongoing benchtop studies and computational fluid modeling have allowed us to reduce the size of our pump while optimizing flow and pressure gradients.

To determine the system's acute hemodynamic effects, we deployed the pumps into seven large animals using an esmolol cardiogenic shock model. The results of these studies showed significant increases in cardiac output, stroke volume, and ejection fraction.

Figure 36:
FIG. 36 shows a computer simulation of auto-entrainment in a flow loop.

Beyond the benefits of unloading the heart, we also found that the intravascular pumping module increased pressure to the renal artery by 28% and increased renal blood flow by 25% compared to controls (FIG. 36). Treatment guidelines to prevent MOF strongly emphasize the importance of maintaining pressure and flow to the end organs and we believe our device is uniquely suited to perform this task.

Figure 37:
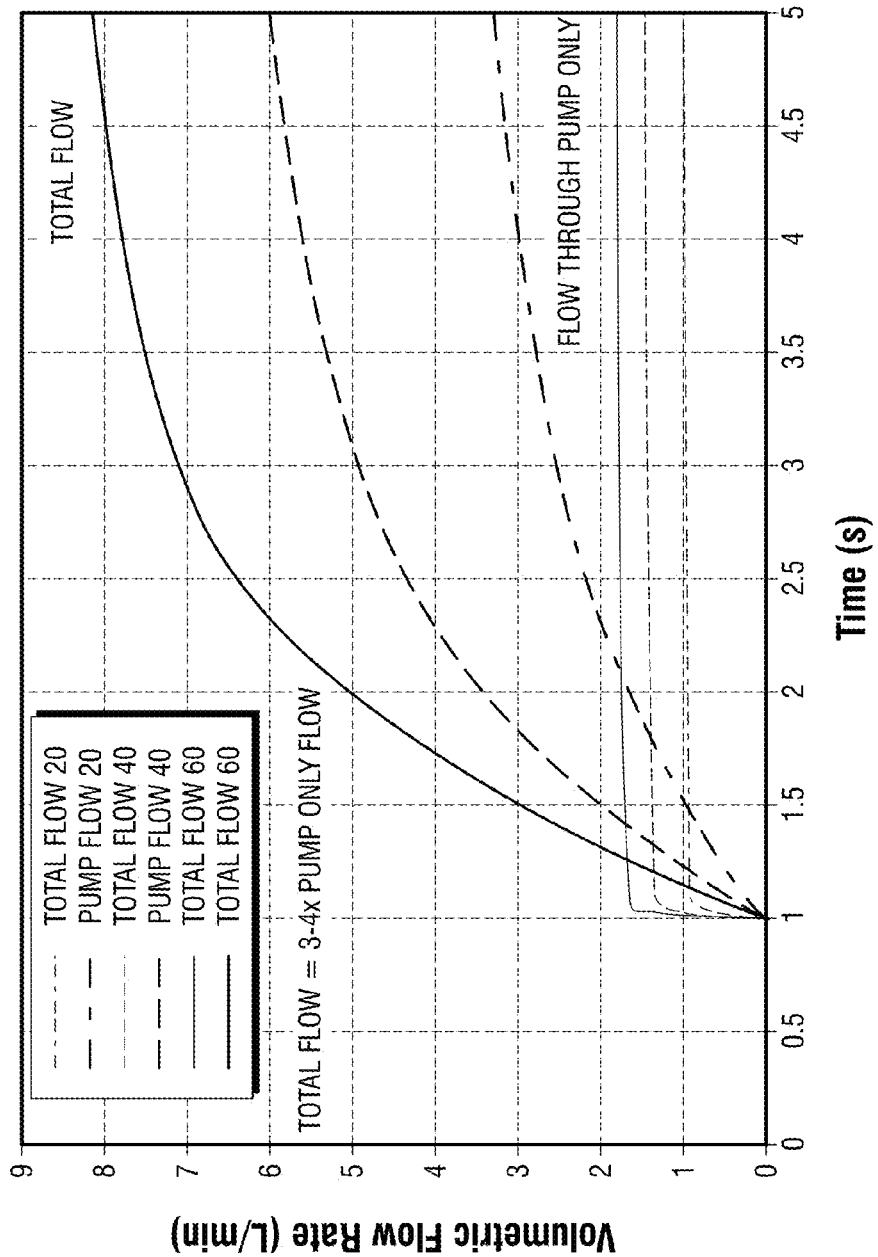
FIG. 37 shows results of a computer simulation of auto-entrainment.

Supporting Data: The hypothesis that increased pressure and flow in the aorta will benefit end organ function is supported by previous research done at the Texas Heart Institute using surgically implanted Left Ventricular Assist Devices (LVADs) in a hemorrhagic shock model. This research, investigated the novel use of an LVAD in combination with conventional fluid and blood resuscitation therapy. They found that LVAD support after prolonged hemorrhagic shock led to significant improvements in survival, markers of end-organ function, and markers of inflammation and anaerobic metabolism (FIG. 37). In addition to markers of organ function, byproducts of anaerobic metabolism as well as levels of inflammatory markers have been shown to correlate with clinical severity and prognosis.

Implementations described herein are included to demonstrate particular aspects of the present disclosure. It should be appreciated by those of skill in the art that the implementations described herein merely represent exemplary implementation of the disclosure. Those of ordinary skill in the art should, in light of the present disclosure, appreciate that many changes can be made in the specific implementations described and still obtain a like or similar result without departing from the spirit and scope of the present disclosure. From the foregoing description, one of ordinary skill in the art can easily ascertain the essential characteristics of this disclosure, and without departing from the spirit and scope thereof, can make various changes and modifications to adapt the disclosure to various usages and conditions. The implementations described hereinabove are meant to be illustrative only and should not be taken as limiting of the scope of the disclosure.

What is claimed is:

1. A system for adjusting fluid flow or pressure within a human body, said system comprising:
   a first pump implantable in vessel of the human body;
   a plurality of struts connected to a housing of said first pump, wherein said struts secure the first pump in a desired location of said vessel and allow substantially unobstructed flow of blood around the first pump;
   one or more inlet ports disposed on said first pump, wherein said inlet ports direct inlet blood flow through the pump, and bypass blood flow is directed around the pump; and
   one or more outlet ports disposed on said first pump, wherein said outlet ports direct at least one high-velocity jet of output blood flow from the pump, and the output blood flow auto-entrains the bypass blood flow to form downstream blood flow.

2. The system of claim 1, wherein flow modification elements are disposed at an intermediate position of the first pump between the one or more inlet ports and the one or more outlet ports.

3. The system of claim 2, wherein at least one of the flow modification elements has a collapsed configuration and a deployed configuration.

4. The system of claim 1, wherein said first pump is positioned in an axis-intersecting or skewed position.

5. The system of claim 4, wherein the first pump is positioned to direct flow to said desired organ or desired region.

6. The system of claim 1, wherein the one or more outlet ports are positioned to direct all pump output flow in a direction opposite a native flow direction.

7. The system of claim 1, wherein said first pump is unidirectional and configured to pump in a direction opposite a native flow direction.

8. The system of claim 1, further comprising a second pump positioned to pump in a direction opposite a pumping direction of the first pump.

9. The system of claim 8, wherein a first outlet of the first pump and a second outlet of the second pump face away from each other.

10. The system of claim 8, wherein a first outlet of the first pump and a second outlet of the second pump face towards each other.

11. The system of claim 1, wherein the system reduces aortic root pressure.

12. The system of claim 1, wherein the system increases pressure in the abdominal aorta.

13. The system of claim 1, wherein the system minimizes reverse bypass flow.

14. The system of claim 1, wherein the one or more outlet ports comprise an inducement nozzle that draws native flow into the center of a lumen surrounded by the at least one high-velocity jet.

* * * * *